(12) United States Patent
Kolonia et al.

(10) Patent No.: US 11,279,549 B2
(45) Date of Patent: *Mar. 22, 2022

(54) TELESCOPING SYRINGE WITH ONE-WAY VALVE

(71) Applicant: New Product Development Concepts LLC, Alpha, NJ (US)

(72) Inventors: Robert A. Kolonia, Milford, NJ (US); Brian J. Kolonia, Bath, PA (US)

(73) Assignee: New Product Development Concepts LLC, Alpha, NJ (US)

( * ) Notice: Subject to any disclaimer, the term of this patent is extended or adjusted under 35 U.S.C. 154(b) by 3 days.

This patent is subject to a terminal disclaimer.

(21) Appl. No.: 17/008,777

(22) Filed: Sep. 1, 2020

(65) Prior Publication Data

US 2020/0399047 A1 Dec. 24, 2020

Related U.S. Application Data

(63) Continuation of application No. 16/291,293, filed on Mar. 4, 2019, now Pat. No. 10,800,597, which is a (Continued)

(51) Int. Cl.
*B65D 83/00* (2006.01)
*B05C 17/005* (2006.01)
(Continued)

(52) U.S. Cl.
CPC ....... *B65D 83/0022* (2013.01); *A61M 5/3134* (2013.01); *A61M 5/3145* (2013.01);
(Continued)

(58) Field of Classification Search
CPC .......... B65D 83/0022; B05C 17/00576; B05C 17/00593; A61M 5/3145; A61M 5/3134;
(Continued)

(56) References Cited

U.S. PATENT DOCUMENTS 1,174,673 A * 3/1916 Bye ............................... 604/236
5,785,682 A * 7/1998 Grabenkort ........... A61M 5/284
604/191

(Continued)

*Primary Examiner* — Paul R Durand
*Assistant Examiner* — Randall A Gruby
(74) *Attorney, Agent, or Firm* — Michael Crilly, Esquire

(57) ABSTRACT

A telescoping syringe suitable for use with medications and other materials is presented. The telescoping syringe includes a valve, a plunger, and a barrel. The valve further includes a barrier, an outlet(s) through the barrier, and an annular extension extending from the barrier. The plunger further includes an inlet(s) and a first side wall with a proximal wall. The barrel includes a second side wall with a distal wall at one end and an open end at another end. The plunger is extendable from and retractable into the barrel at the open end via slidable engagement between first and second walls. The valve directly contacts one end of the first wall so that an annular flange slidingly engages an annular groove. The valve and the barrel slidingly contact the plunger so as to open and to close the inlet(s) and/or the outlet(s). The inlet(s) in the open position permits gas to enter a first reservoir within the plunger as fluid is transferred from the first reservoir through the outlet(s) in the open position to a second reservoir within the barrel.

23 Claims, 21 Drawing Sheets

Related U.S. Application Data continuation-in-part of application No. 15/827,652, filed on Nov. 30, 2017, now Pat. No. 10,450,124, which is a continuation-in-part of application No. 15/504,678, filed as application No. PCT/US2016/046958 on Aug. 15, 2016, now Pat. No. 9,850,058.

(60) Provisional application No. 62/217,352, filed on Sep. 11, 2015.

(51) Int. Cl.
*A61M 5/315* (2006.01)
*A61M 5/31* (2006.01)
*B65D 81/32* (2006.01)
*A61M 5/19* (2006.01)

(52) U.S. Cl.
CPC ... *A61M 5/31511* (2013.01); *B05C 17/00593* (2013.01); *B65D 81/3255* (2013.01); *A61M 5/19* (2013.01); *A61M 2005/3128* (2013.01); *A61M 2005/3131* (2013.01); *A61M 2005/31518* (2013.01); *A61M 2205/0216* (2013.01)

(58) Field of Classification Search
CPC ............ A61M 5/3135; A61M 5/31513; A61M 2005/31518; A61M 2005/3131; A61M 2005/3128; A61M 5/31596
See application file for complete search history.

(56) References Cited

U.S. PATENT DOCUMENTS

| | | | | |
|---|---|---|---|---|
| 6,080,131 | A * | 6/2000 | Van Der Meyden | A61M 5/284 604/82 |
| 6,193,695 | B1 * | 2/2001 | Rippstein, Jr. | A61M 5/315 604/110 |
| 6,508,792 | B2 * | 1/2003 | Szames | A61M 5/3134 604/218 |
| 6,602,223 | B2 * | 8/2003 | Szapiro | A61M 5/284 604/89 |
| 8,632,519 | B2 * | 1/2014 | Lum | A61M 5/31515 604/506 |
| 9,180,249 | B2 * | 11/2015 | Hallahan | A61M 5/19 |
| 2003/0040701 | A1 * | 2/2003 | Dalmose | A61M 5/31596 604/87 |
| 2014/0276442 | A1 * | 9/2014 | Haughey | A61M 5/19 604/191 |
| 2015/0025456 | A1 * | 1/2015 | Shetty | A61M 5/31515 604/91 |
| 2020/0171243 | A1 * | 6/2020 | Villain | A61M 5/3134 |
| 2020/0179167 | A1 * | 6/2020 | Bryant | A61M 5/28 |

* cited by examiner

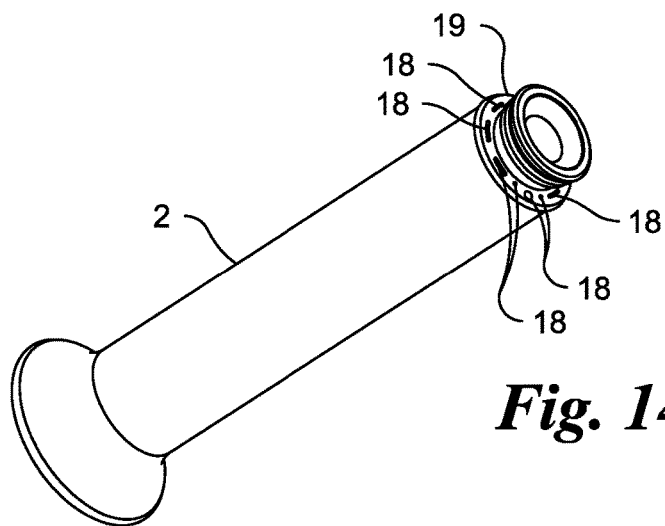
*Fig. 14a*
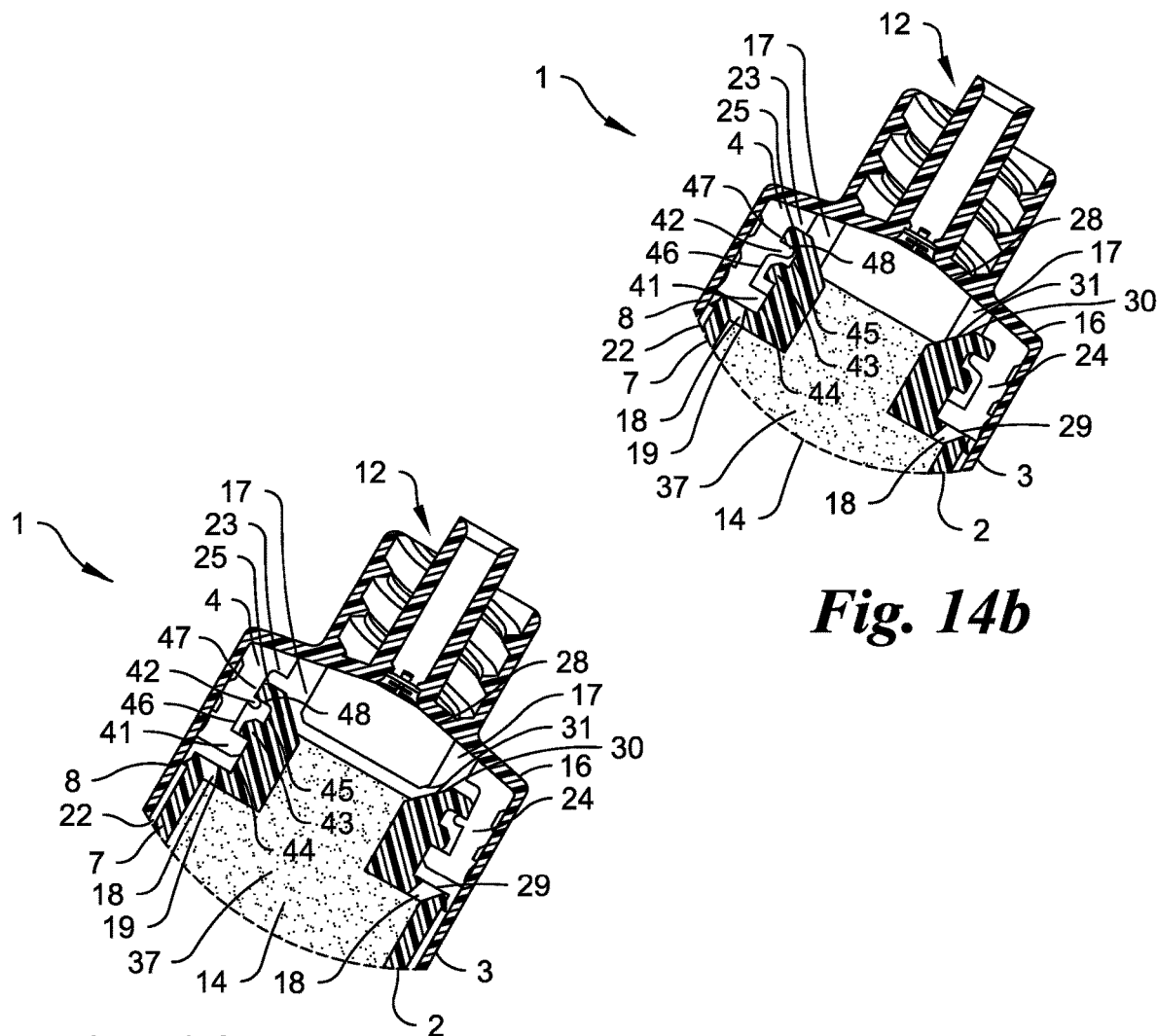
*Fig. 14b*
*Fig. 14c*

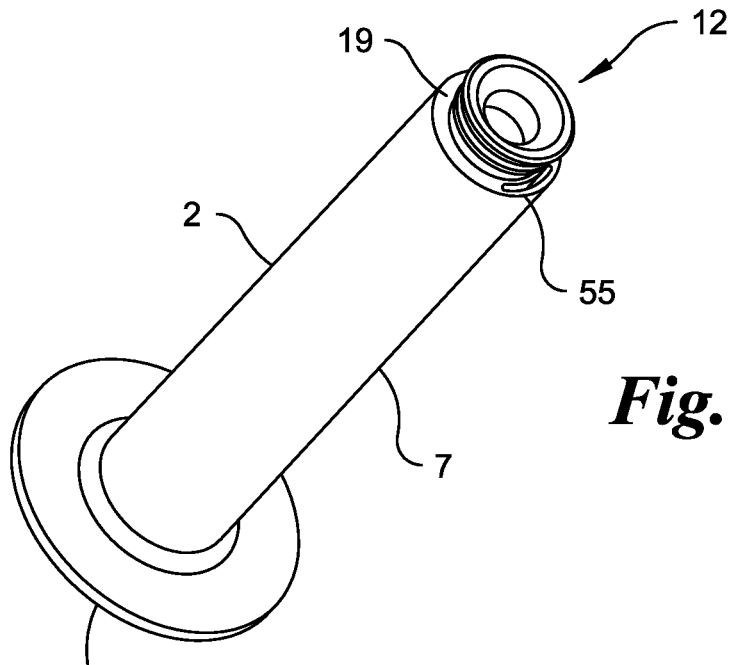
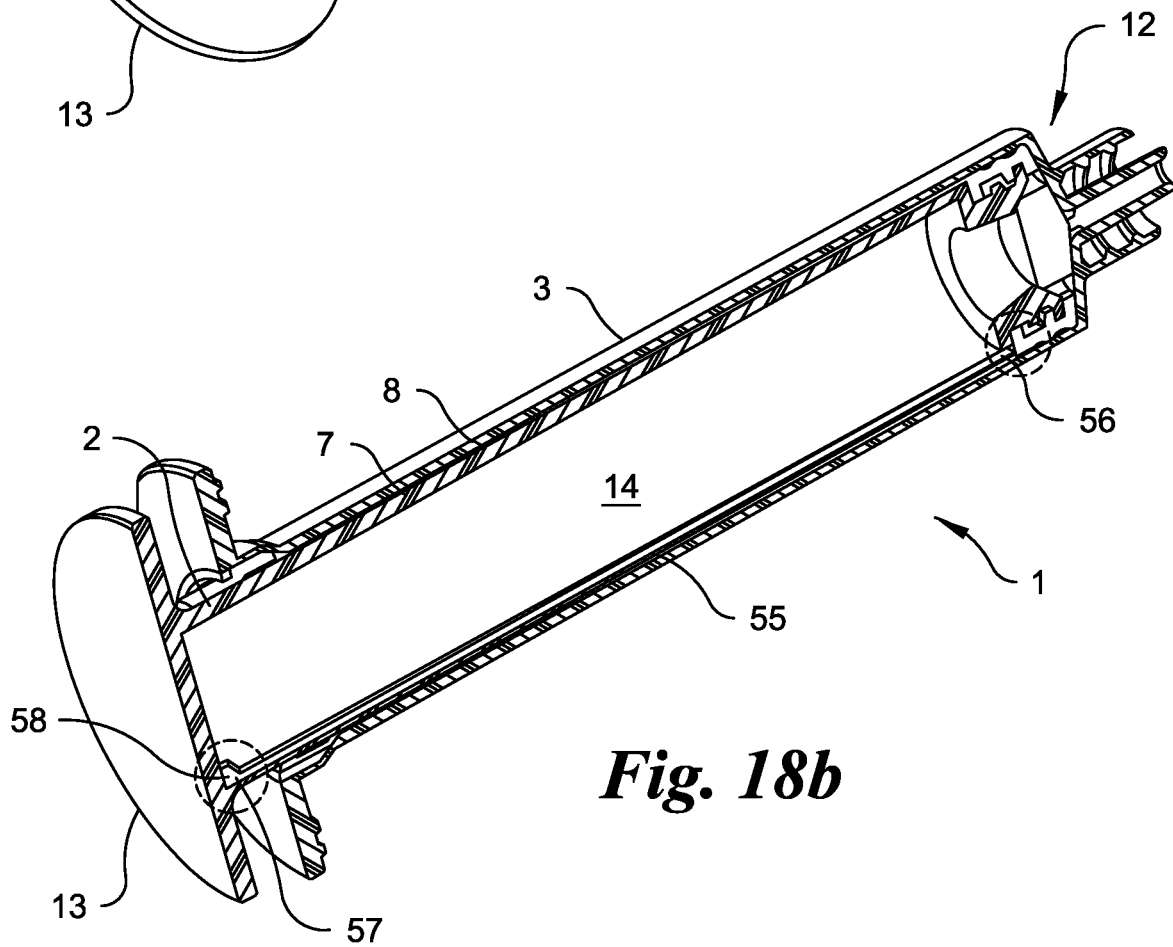

TELESCOPING SYRINGE WITH ONE-WAY VALVE

CROSS REFERENCE TO RELATED APPLICATIONS

This application is a continuation of U.S. Non-Provisional application Ser. No. 16/291,293 filed Mar. 4, 2019 which is a continuation-in-part of U.S. Non-Provisional application Ser. No. 15/827,652 filed Nov. 30, 2017 now U.S. Pat. No. 10,450,124 which a continuation-in-part of U.S. Non-Provisional application Ser. No. 15/504,678 filed Feb. 17, 2017 now U.S. Pat. No. 9,850,058 which is a National Phase of PCT Application No. PCT/US2016/046958 filed Aug. 15, 2016 which further claims priority from U.S. Provisional Application No. 62/217,352 filed Sep. 11, 2015, each entitled Telescoping Syringe with One-Way Valve. The subject matters of the prior applications are incorporated in their entirety herein by reference thereto.

FEDERALLY SPONSORED RESEARCH AND DEVELOPMENT

None.

BACKGROUND OF THE INVENTION

1. Field of the Invention

The invention generally relates to a telescoping syringe with a plunger extendible from and retractable into a barrel and more particularly is concerned, for example, with a valve mechanism facilitating flow between reservoirs within a syringe. Specifically, the valve is extendible from and retractable onto one end of the plunger. The valve prevents leakage of a fluid from the syringe prior to extension of the plunger from the barrel. The valve also permits transfer of a fluid from a first reservoir within the plunger into a second reservoir within the barrel during extension of the plunger from the barrel. The valve further facilitates ejection of a fluid from the second reservoir during retraction of the plunger into the barrel.

2. Background

A variety of telescoping syringes are known within the art. Conventional syringes are often used in connection with a vial containing a fluid, typically a medication or other injectable or ejectable fluid, whereby the user draws fluid into the syringe. It is common for some syringes to be packaged as prefilled devices, whereby a syringe is sold to the end user prefilled with fluid already residing within the syringe. Prefilled syringes are beneficial in that such devices eliminate one or more steps required for proper use thereby reducing the cost of use and in that such devices control the quantity of fluid delivered thereby reducing errors associated with use.

However, prefilled syringes and packaging therefore tend to be bulky because the barrel is filled with fluid requiring the plunger to extend from the barrel. The elongated nature of prefilled syringes and packaging therefore increases non-use costs associated with shipping and storage by virtue of the greater volume occupied by the prefilled device.

Medical applications of prefilled syringes are particularly problematic in that the fluid contained within the syringe often must be safeguarded from theft via storage within a locked cabinet or the like. The space available for secured storage is often limited and costly, thus creating a need for prefilled syringes to have a smaller footprint with and without packaging.

It is further understood that the related arts do not provide a mechanism that reliably and simply facilitates proper function of a telescoping syringe. For example, known telescoping syringes are mechanically complex in design and use, functionally unreliable, difficult to manufacture, and/or costly. Furthermore, known telescoping syringes are prone to leakage and unable to prevent or minimize air surrounding the syringe from entering a second or ejection reservoir as fluid is transferred from a first or storage reservoir to the ejection reservoir.

For at least the reasons discussed above, the benefits and advantages of telescoping-type syringes have yet to be completely realized.

Accordingly, what is required is a telescoping syringe that is mechanically simple in design and use, functionally reliable, easily manufactured, and less costly to package, ship, store and use.

SUMMARY OF THE INVENTION

An object of the invention is to provide a telescoping syringe that is mechanically simple in design and use, functionally reliable, easily manufactured, and less costly to package, ship, store and use.

In accordance with some embodiments of the invention, the telescoping syringe includes a one-way valve, a plunger, and a barrel. The one-way valve further includes a barrier, at least one outlet through the barrier, and an annular extension extending from one side of the barrier. The annular extension is disposed about the outlet(s). The plunger further includes a proximal wall fixed at a proximal end of a first side wall and at least one inlet. The one-way valve directly contacts a distal end of the first side wall so that an annular flange extending inward from the annular extension slidingly engages an annular groove along an outer surface of the first side wall between a first position defined by a proximal shoulder extending outward from the first side wall and a second position defined by a distal shoulder extending outward from the first side wall. The circumferential end of the first side wall contacts the barrier to close the outlet(s) when the annular flange is biased toward the first position. The circumferential end does not contact the barrier to open the outlet(s) when the annular flange is biased toward the second position. A first reservoir is defined by the first side wall, the proximal wall, and the one-way valve. The inlet(s) permits a gas to enter the first reservoir as a fluid is transferred through the one-way valve to a second reservoir. The barrel further includes a second side wall with a nipple fixed to a distal wall at one end and an open end at another end. The plunger is extendable from and retractable into the barrel at the open end via slidable engagement between the first side wall and the second side wall. The second reservoir is defined by the distal wall, the second side wall, and the one-way valve when the plunger is extended from the barrel.

In accordance with other embodiments, the inlet(s) is disposed along the proximal wall.

In accordance with other embodiments, the inlet(s) is formed by a check valve secured within an opening along the proximal wall. The check valve prevents the gas from exiting the first reservoir when the fluid is transferred out of the second reservoir as the plunger is retracted into the barrel.

In accordance with other embodiments, the inlet(s) is disposed along the first side wall.

In accordance with other embodiments, an annular sealing ring disposed along the second side wall sealingly engages the inlet(s) when the plunger is fully retracted within the barrel.

In accordance with other embodiments, the annular sealing ring does not sealingly engage the inlet(s) when the plunger is extended from the barrel.

In accordance with other embodiments, the gas enters the plunger at one location and then the gas enters the first reservoir at another location.

In accordance with other embodiments, the inlet(s) partially traverses the first side wall from the first reservoir to a passageway. The passageway passes through the first side wall from the proximal shoulder to the inlet(s). The passageway is closed when the valve is retracted onto the plunger so that the proximal shoulder contacts the annular extension. The passageway is open when the valve is extended from the plunger so that the proximal shoulder does not contact the annular extension.

In accordance with other embodiments, a gap is disposed between the first side wall and the second side wall. The gas does not pass through the gap into the passageway when the passageway is closed. The gas passes through the gap into the passageway when the passageway is open.

In accordance with other some embodiments, the telescoping syringe includes a valve, a plunger, and a barrel. The valve further includes a barrier, at least one outlet through the barrier, and an annular extension extending from one side of the barrier about the outlet(s). The plunger further includes a first side wall and a proximal shoulder disposed along the first side wall. At least one inlet traverses the first side wall adjacent to the annular extension. The valve contacts the first side wall adjacent to the proximal shoulder so that an annular flange slidingly engages an annular groove between first and second positions. The first side wall contacts the barrier at the first position to close the outlet(s) and does not contact the barrier when not at the first position to open the outlet(s). The annular extension contacts the proximal shoulder at the first position to close the inlet(s) and does not contact the proximal shoulder when not at the first position to open the inlet(s). A first reservoir is disposed within the plunger. The barrel further includes a nipple fixed at one end of a second side wall. The plunger is slidingly extendable from and slidingly retractable into the barrel at another end of the second side wall. A second reservoir is disposed within the barrel when the plunger is extended from the barrel. A gas enters the first reservoir via the inlet(s) as a fluid passes from the first reservoir to the second reservoir via the outlet(s) when the annular flange and the annular groove are no longer configured at the first position.

In accordance with other embodiments, the inlet(s) is disposed along the proximal shoulder.

In accordance with other embodiments, the inlet(s) is disposed along the annular groove.

In accordance with other embodiments, a break-away valve is disposed within the nipple.

In accordance with other embodiments, a diaphragm is attached to the barrel for sealing the nipple prior to ejection of the fluid from the second reservoir.

In accordance with other embodiments, at least one stop is disposed within the nipple which permits the fluid to traverse and exit the nipple.

In accordance with other embodiments, a filter element is disposed along the telescoping syringe which filters the gas prior to entering the inlet(s).

In accordance with other embodiments, a biasing mechanism permits the one-way valve to extend from the plunger when the plunger is extended from the barrel and then causes the one-way valve to retract onto the plunger.

In accordance with other embodiments, the biasing mechanism includes an elastic annular flange along the one-way valve which interacts with a shoulder along the plunger.

As described herein, the telescoping syringe includes a barrel and a plunger. The plunger further includes a one-way valve at a distal end thereof and a first reservoir therein. The plunger is disposed within the barrel so that the plunger is extendable from and retractable into the barrel. The valve prevents gas from leaking into the first reservoir and fluid from leaking out of the first reservoir prior to use of the syringe. The valve simultaneously permits the gas to fill the first reservoir and the fluid to exit the first reservoir during extension of the plunger from the barrel. The valve also prevents the gas from exiting the first reservoir and the fluid from reentering the first reservoir during retraction of the plunger into the barrel.

A user pulls on one end of the plunger to extend or telescope the plunger from the barrel. The one-way valve permits the fluid within the first reservoir to pass through the valve and to fill a second reservoir within the barrel. The second reservoir is formed during extension of the plunger from the barrel so that the volume of the second reservoir is approximately equal to the volume vacated by the plunger. Gas fills the plunger as the fluid moves from the plunger into the barrel. The user then depresses the plunger causing the plunger to retract into the barrel so that the fluid now residing in the second reservoir exits the syringe via a nipple at the distal end of the syringe.

The valve is attached to the plunger in an extendable/retractable arrangement. The valve includes a substantially circular-shaped barrier or wall and an annular extension therefrom, the latter attached to and extending from the outer circumference of the barrier. The barrier further includes one or more outlets positioned to align with the circumferential end of a side wall along the plunger.

The plunger is disposed within the barrel prior to use of the syringe so that the one-way valve is adjacent to the nipple part of the syringe. The valve contacts the barrel adjacent to the nipple along the barrel thereby sealing the front end of the syringe to prevent leakage of atmosphere surrounding the syringe into and fluid within the syringe from the syringe. The valve is slidably seated onto the circumferential end of the plunger so as to align with and cover the outlets, thereby closing and sealing the outlets, when the valve is seated onto the plunger. This arrangement prevents the gas from entering and fluid from exiting the plunger prior to use. The annular extension also overlays and covers optional inlets adjacent to the valve, thereby closing and sealing the inlets, when the valve is retracted onto the plunger. This arrangement prevents the gas from exiting from and fluid from reentering the first reservoir.

When the plunger is extended from the barrel, a lower pressure is formed within the barrel adjacent to the nipple causing the valve to extend from the plunger thereby separating the circumferential end from the outlets and allowing fluid within the first reservoir, residing within the plunger, to flow into the second reservoir, residing within the barrel, via the outlets. Extension of the valve also exposes optional inlets along the side wall of the plunger adjacent to the valve thereby allowing a gas surrounding the syringe to enter the first reservoir as fluid in transferred from the first reservoir into the second reservoir. One or more inlets along the plunger adjacent to the valve and/or along or adjacent to the proximal end of the plunger may permit the gas to flow into the plunger during fluid transfer. The plunger is extended so that at least a portion of the fluid is transferred from the first reservoir to the second reservoir.

Formation of the lower pressure within the second reservoir is possible when the flow of gas into the second reservoir is restricted during extraction of the plunger from the barrel. Gas flow into the second reservoir via the nipple is avoided by either a removable cap attached to the nipple or a valve-mechanism adjacent to the nipple. Gas flow into the second reservoir via a gap or space between the side walls of the plunger and barrel is also avoided by a seal between the inner diameter of the barrel and outer diameter of the valve. The valve may include one or more concave and/or convex ridges that extend therefrom and slidingly contact the inner diameter of the barrel thereby defining a slidable seal.

When the plunger is retracted into the barrel, the valve retracts onto the plunger closing both optional inlets and outlets adjacent to the valve so as to prevent fluid from reentering and gas from exiting the first reservoir. The fluid within the second reservoir along the barrel flows into and through the nipple as the plunger is retracted into the barrel. The plunger is retracted so that at least a substantial portion of the fluid is ejected from the second reservoir.

In some applications, the plunger may be partially extended from the barrel during use so that less than all fluid is transferred from the first reservoir into the second reservoir. The plunger is then retracted into the barrel so that less than all fluid contained within the syringe is ejected from the second reservoir. The extension and retractions steps may be repeated until all fluid is expelled from the syringe. This functionality facilitates a multi-use capability by the invention. The syringe may include indicia or other markings that permit a user to transfer the desired amount from the first reservoir to the second reservoir for each transfer/ejection cycle.

A valve-like seal may be beneficial in some embodiments when a cap is not secured to the nipple prior to extension of the plunger. An optional break-away valve may be attached to the one-way valve to achieve a lower pressure region adjacent to the nipple and the one-way valve prior to extension of the plunger. The break-away valve may seal the nipple before and during extension of the plunger. The break-away valve may also seal the nipple as fluid is transferred from the first reservoir to the second reservoir. When the plunger is retracted, the break-away valve may traverse a portion of the nipple so as to engage stops within the nipple which permit the fluid to exit the syringe but not the break-away valve.

An optional filter may be advantageous in some embodiments along the interface between the side walls of the plunger and the barrel. A pocket is provided along the side wall of the barrel, preferably adjacent to the proximal end of the syringe. The pocket is sized so that a filter element may be secured between the side walls without impeding the sliding motion required between the barrel and the plunger for proper function of the syringe. The filter element communicates with a gap between the side walls so as to permit the gas to pass through the filter and then traverse the gap in the direction of the valve. The filtered gas enters the first reservoir via the inlets thereby replacing the fluid transferred to the second reservoir so as to avoid a vacuum within the first reservoir.

In other embodiments, it may be advantageous for the valve to include a biasing mechanism that retracts and reseats the valve onto the plunger. The biasing mechanism may be a device that is functionally similar to a spring. In preferred embodiments, the biasing mechanism is deformable, yet resilient so as to allow the biasing mechanism to elastically deform during extension of the plunger and elastically recovers its original shape after the plunger is extended to the desired length and/or the desired quantity of liquid is transferred from the first reservoir to the second reservoir. One non-limiting example of a biasing mechanism is an elastic annular flange along the valve which interacts with a shoulder along the plunger.

In its simplest form, the invention may be comprised of three components, namely, a plunger, a barrel, and a one-way valve, each composed of a plastic molded via injection molding techniques understood in the art. However, other materials and manufacturing methods are likewise suitable to the present invention. The invention is readily manufacturable, user friendly, functionally reliable, and a cost-effective alternative to the various telescoping syringe designs currently known within the art. The invention provides a compact form by virtue of the plunger retracted into the barrel prior to use which in turn reduces packaging, shipping, and storage costs. The retracted arrangement of the plunger prior to use also avoids accidental ejection of fluid from the syringe when the syringe is inadvertently dropped prior to extension of the plunger from the barrel. The invention is compatible with and applicable to injectable and ejectable fluids suitable to prefilled syringes sold to users as a self-contained and fully-functional product. The valve mechanism allows end users to selectively dispense less than all fluid contained within the plunger thereby facilitating multi-use capability.

The above and other objectives, features, and advantages of the preferred embodiments of the invention will become apparent from the following description read in connection with the accompanying drawings, in which like reference numerals designate the same or similar elements.

BRIEF DESCRIPTION OF THE DRAWINGS

Additional aspects, features, and advantages of the invention will be understood and will become more readily apparent when the invention is considered in the light of the following description made in conjunction with the accompanying drawings.

FIG. 14a is a perspective view illustrating a plunger with at least one inlet disposed along a proximal shoulder in accordance with an embodiment of the invention.

FIG. 14b is an enlarged cross-section view illustrating a valve with a biasing mechanism prior to extension of the plunger from a barrel whereby the valve is disposed in a closed configuration which prevents a fluid from exiting a first reservoir within the plunger via an inlet(s) along a proximal shoulder of a side wall and via an outlet(s) along the valve in accordance with an embodiment of the invention.

FIG. 14c is an enlarged cross-section view illustrating a valve with a biasing mechanism after extension of the plunger from the barrel whereby the valve is disposed in an open configuration to permit gas to enter the first reservoir via the inlet(s) and to permit transfer of the fluid from the first reservoir within the plunger to a second reservoir within the barrel via the outlet(s) in accordance with an embodiment of the invention.

FIG. 18a is a perspective view illustrating one end of a passageway within a side wall of a plunger for a telescoping syringe in accordance with an embodiment of the invention.

FIG. 18b is a cross-section view illustrating the passageway disposed within the side wall so as to communicate a gas from a distal end of the plunger to a proximal end of the plunger thereby permitting a gas to fill a first reservoir within the plunger as fluid exits the plunger in accordance with an embodiment of the invention.

DETAILED DESCRIPTION OF THE INVENTION

Figure 1:
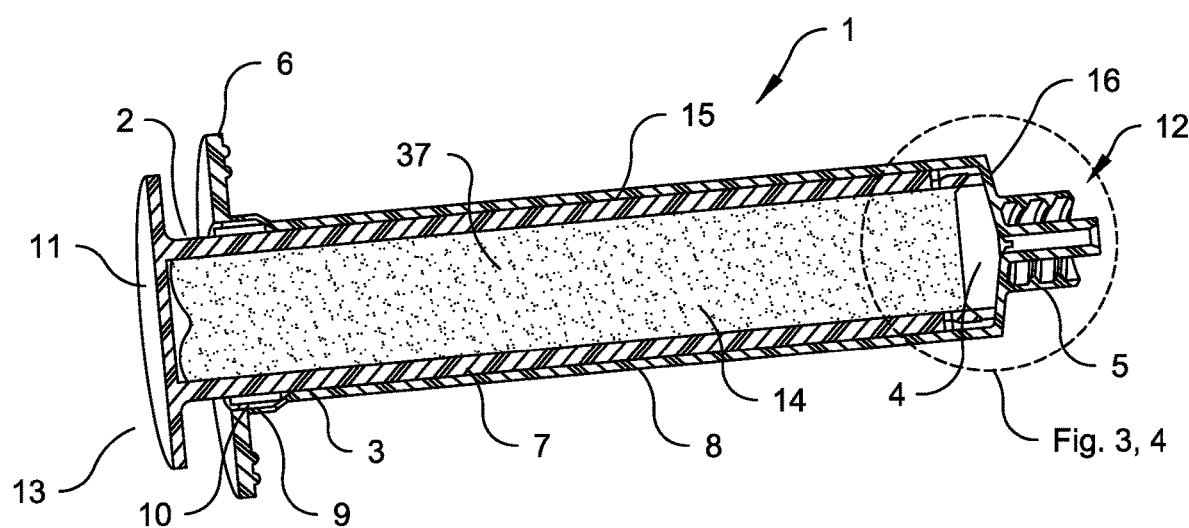
FIG. 1 is a perspective cross-section view illustrating a telescoping syringe including a barrel, a plunger, and a valve prior to extension of the plunger from the barrel in accordance with an embodiment of the invention.

Reference will now be made in detail to several embodiments of the invention that are illustrated in the accompanying drawings. Wherever possible, same or similar reference numerals are used in the drawings and the description to refer to the same or like parts. The drawings are in simplified form and are not to precise scale.

While features of various embodiments are separately described herein, it is understood that such features may be combinable to form other additional embodiments.

Components described herein are manufactured via methods, processes, and techniques understood in the art, including, but not limited to, machining, molding, forming, and three-dimensional printing. Components may be composed of any suitable material including, but not limited to, injection moldable thermoplastics.

Referring now to FIG. 1, the syringe 1 includes a plunger 2, a barrel 3, and a valve 4. The plunger 2 is a tube-shaped element with a cavity therein defined by a substantially cylindrical-shaped side wall 7 with a substantially planar-shaped proximal wall 11 at a first end thereof and an opening at a second end thereof. The barrel 3 is a tube-shaped element with a cavity therein defined by a substantially cylindrical-shaped side wall 8 with a distal wall 16 at one end thereof and an opening at a second end thereof. The inner diameter of the barrel 3 and outer diameter of the plunger 2 are sized so as to allow a slidable engagement therebetween. This arrangement permits insertion of the plunger 2 into the barrel 3 and extension of the plunger 2 from the barrel 3. The proximal wall 11 is positioned at the proximal end 13 of the syringe 1. A flange 6 extends from the barrel 3 adjacent to the proximal end 13. The flange 6 and the proximal wall 11 are shaped to allow a user to pull and extend the plunger 2 from the barrel 3 and to push and retract the plunger 2 into the barrel 3. The distal wall 16 is positioned adjacent to the distal end 12 of the syringe 1. A nipple 5 extends from the distal wall 16.

Referring again to FIG. 1, the valve 4 is secured to the second end of the side wall 7 along the plunger 2 adjacent to the distal wall 16. The valve 4, side wall 7, and proximal wall 11 define a cavity referred to as the first reservoir 14. The first reservoir 14 is initially sealed as discussed herein to contain a fluid 37. The volume occupied by the plunger 2 within the barrel 3 further generally defines a second reservoir 15. The actual volume of the second reservoir 15 is defined by the volume bounded by the side wall 8, distal wall 16, and valve 4. The second reservoir 15 has no or minimal actual volume when the plunger 2 is retracted into the barrel 3. As the plunger 2 is extended from the barrel 3, the actual volume of the second reservoir 15 increases proportional to the length of the plunger 2 extended from the barrel 3. In preferred embodiment, the volume of the second reservoir 15 should be substantially comparable to the volume of the first reservoir 14 when the plunger 2 is substantially extended from the barrel 3.

Figure 2:
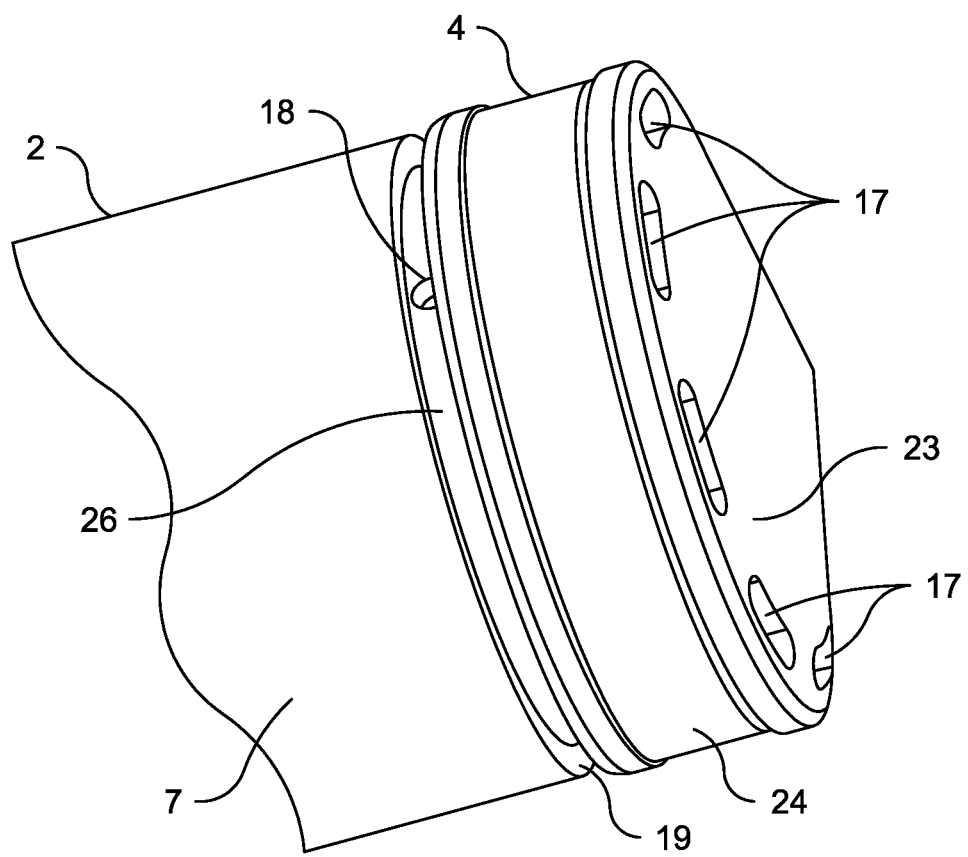
FIG. 2 is an enlarged perspective view illustrating a valve extendible from and retractable onto one end of a plunger whereby the valve includes at least one outlet and the plunger includes at least one optional inlet in accordance with an embodiment of the invention.
Figure 3:
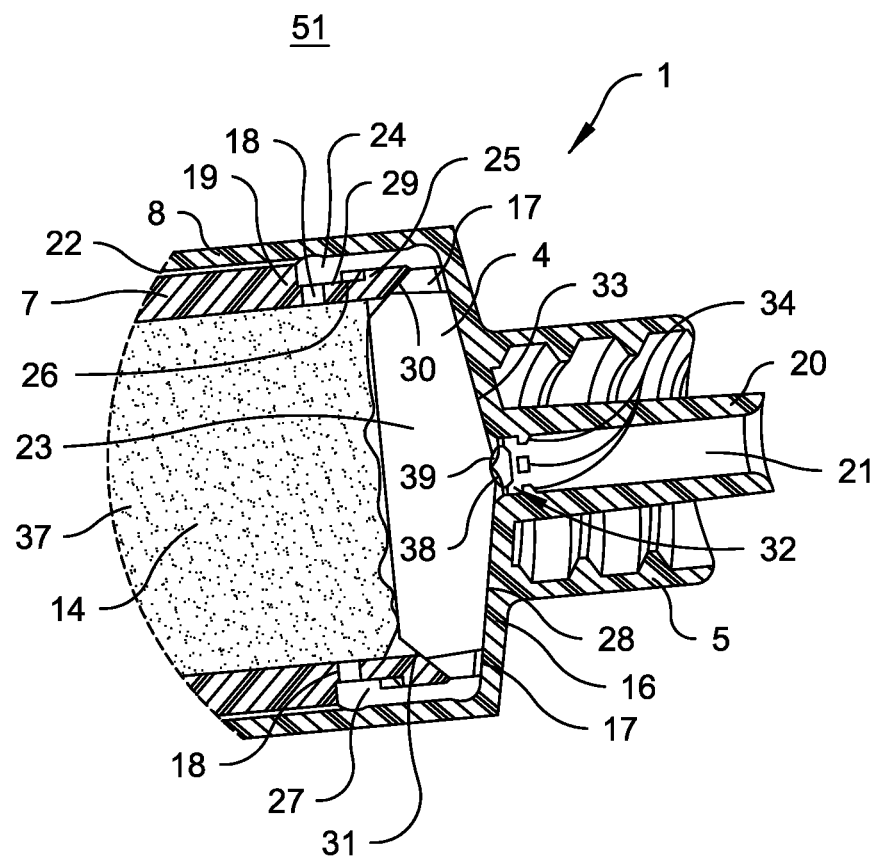
FIG. 3 is an enlarged cross-section view illustrating a valve prior to extension of a plunger from a barrel whereby the valve is disposed in a closed configuration to prevent escape of a fluid from a first reservoir within the plunger in accordance with an embodiment of the invention.
Figure 4:
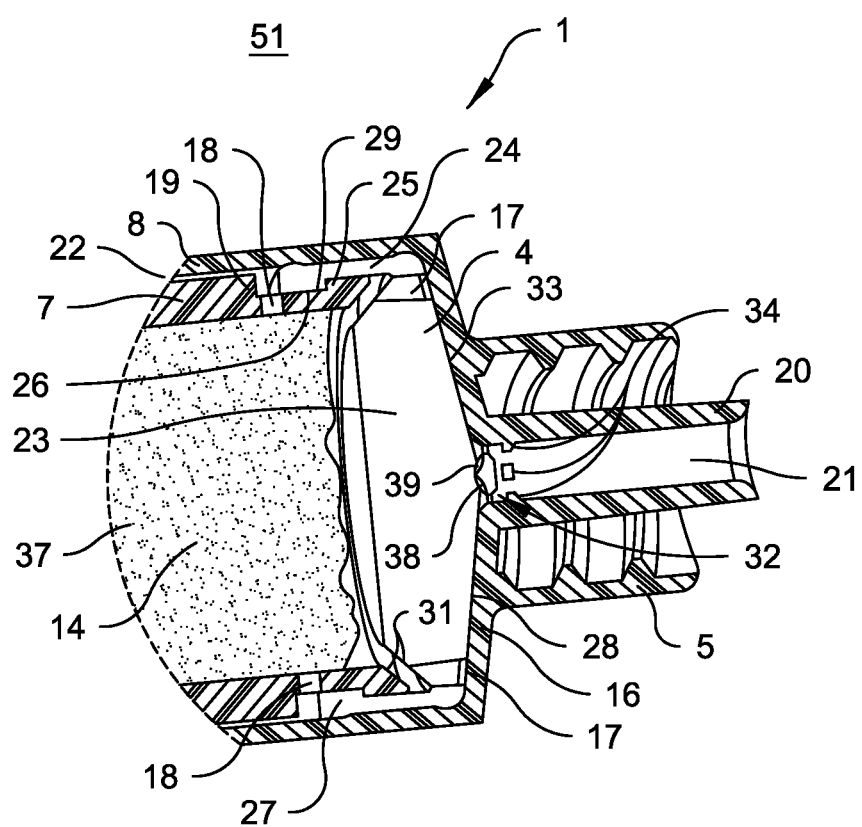
FIG. 4 is an enlarged cross-section view illustrating a valve after initial extension of a plunger from a barrel whereby the valve is extended from the plunger and disposed in an open configuration to permit a gas to enter a first reservoir and to permit transfer of a fluid from the first reservoir within the plunger to a second reservoir within the barrel in accordance with an embodiment of the invention.

Referring now to FIGS. 2-4, the valve 4 includes a disk-shaped barrier 23 and an annular extension 24. The annular extension 24 is a ring-shaped element that extends from the barrier 23 adjacent to the outer circumference of the barrier 23. An annular flange 27 extends radially inward from the annular extension 24. The valve 4 further includes at least one outlet 17 defined by an opening that traverses the thickness of the barrier 23. The outlets 17 are positioned along the barrier 23 so as to align with the circumferential end 30 of the side wall 7 along the plunger 2. The outlets 17 and the side wall 7 are dimensioned so that contact between the circumferential end 30 and the barrier 23 ensures the end surface of the side wall 7 completely covers and thereby seals the outlets 17 when the valve 4 is retracted onto the plunger 2.

Referring again to FIGS. 2-4, the side wall 7 further includes an annular groove 26 bounded by a proximal shoulder 19 and a distal shoulder 25. At least one inlet 18 defined by an opening traversing the thickness of the side wall 7 is provided along the annular groove 26. The inlets 18 communicate with a gap 22 or other comparable opening along or between the side walls 7, 8 to permit a gas 51 adjacent to the syringe 1 to enter the first reservoir 14 as fluid 37 exits therefrom.

Referring again to FIGS. 2-4, the valve 4 is seated onto the side wall 7 so that the annular flange 27 engages the annular groove 26. The dimensions of the annular flange 27 and the annular groove 26 ensure a slidable engagement between the valve 4 and the plunger 2. This arrangement permits the valve 4 to extend from and retract onto plunger 2 within the limits imposed by the proximal shoulder 19 and the distal shoulder 25. The inlets 18, annular groove 26, annular flange 27, proximal shoulder 19, and distal shoulder 25 are arranged so that the annular flange 27 overlays and seals the inlets 18 when the annular flange 27 is biased toward the proximal shoulder 19 and the annular flange 27 does not seal the inlets 18 when the annular flange 27 is biased toward the distal shoulder 25. In preferred embodiments, the outlets 17, circumferential end 30, annular groove 26, annular flange 27, proximal shoulder 19, and distal shoulder 25 are arranged so that the circumferential end 30 overlays and seals the outlets 17 when the annular flange 27 contacts the proximal shoulder 19, as illustrated in FIG. 3, and the circumferential end 30 neither overlays nor seals the outlets 17 when the annular flange 27 contacts the distal shoulder 25, as illustrate in FIG. 4.

The nipple 5 is attached to and extends from the distal wall 16. The nipple 5 includes a port 20 with an opening 21 therethrough. The opening 21 provides a pathway enabling fluid 37 within the second reservoir 15 to exit the syringe 1. The nipple 5 and port 20 may include features or elements that enable attachment of a cap and/or needle to the syringe 1.

Referring again to FIGS. 2-4, the valve 4 provides sealing critical to function of the syringe 1. A first sealing interface 28 is formed by the valve 4 and the distal wall 16. In preferred embodiments, the outer surface of the barrier 23 along the valve 4 contacts the inner surface of the distal wall 16 to form a contact seal that prevents fluid 37 from reaching the nipple 5 prior to extension of the plunger 2. The first sealing interface 28 is closed when the barrier 23 contacts the distal wall 16 and open when the barrier 23 is separated from the distal wall 16. A second sealing interface 29 is formed by the valve 4 and the surface of the side wall 7. In preferred embodiments, the inner circumferential surface of the annular flange 27 slidably contacts the outer circumferential surface of the annular groove 26 so as to overlay the inlets 18 prior to extension of the plunger 2 thereby preventing gas 51 from reaching the fluid 37 and during retraction of the plunger 2 to prevent gas 51 from exiting and fluid 37 from reentering the first reservoir 14. The second sealing interface 29 is closed when the annular flange 27 completely overlays the inlets 18 and open when the annular flange 27 does not completely overlay the inlets 18. A third sealing interface 31 is formed by the valve 4 and the circumferential end 30 of the side wall 7. In preferred embodiments, the circumferential end 30 should contact the barrier 23 so as to overlay the outlets 17 prior to extension of the plunger 2 to prevent fluid 37 from reaching the nipple 5 and during retraction of the plunger 2 to prevent fluid 37 from reentering the first reservoir 14. The third sealing interface 31 is closed when the circumferential end 30 contacts the inside surface of the barrier 23 and open when the circumferential end 30 is separated from the barrier 23.

In some embodiments, the second sealing interface 29 may extend along and include a surface along the proximal shoulder 19 and a surface along the annular extension 24 to the extent that contact is permitted between the surfaces. The second sealing interface 29 along the proximal shoulder 19 is closed when the annular extension 24 contacts the proximal shoulder 19 and is open when the annular extension 24 is pulled away from and no longer contacts the proximal shoulder 19.

Figure 5:
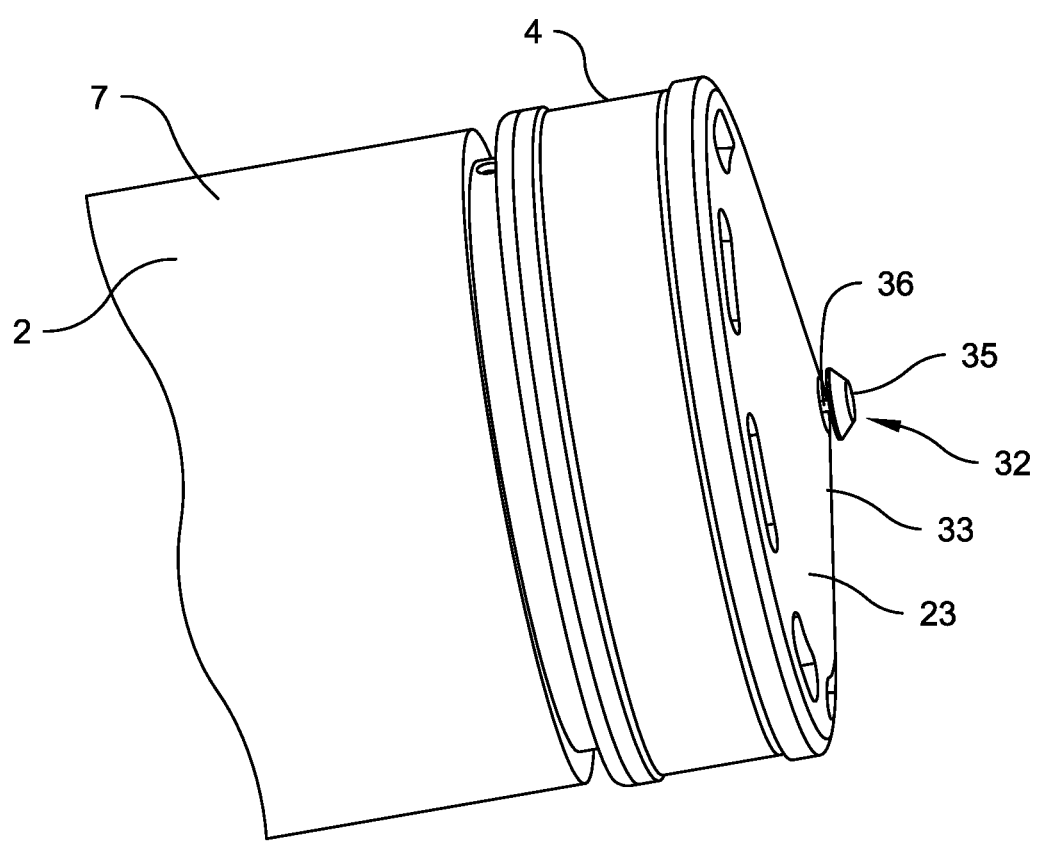
FIG. 5 is an enlarged perspective view illustrating a valve extendible from and retractable onto one end of a plunger whereby the valve is extended from the plunger, the valve includes at least one outlet, the plunger includes at least one optional inlet, and an optional break-away valve is attached to the plunger in accordance with an embodiment of the invention.

Referring now to FIGS. 3-5, an optional break-away valve 32 may be provided along the outer surface 33 of the barrier 23 so as to align with the nipple 5. The break-away valve 32 may include a plug 35 and a stem 36. The plug 35 is generally shaped, dimensioned, and positioned so as to engage the port 20 and seal the opening 21. This arrangement provides a fourth sealing interface 39 between valve 4 and nipple 5 adjacent to the opening 21. The stem 36 is an element which secures the plug 35 to the valve 4, yet remains separable or breakable when extension forces are communicated to the valve 4 via the plunger 2. In one non-limiting example, the stem 36, plug 35, and valve 4 could be molded as a single component. In another non-limiting example, the stem 36 and plug 35 could be separately molded from the valve 4 and either mechanically or adhesively fastened thereto. Regardless of the construction and assembly approaches for the break-away valve 32, the stem 36 should ensure attachment of the plug 35 to the valve 4 prior to extension and should mechanically break or separate from the plug 35 or the valve 4 when the plunger 2 is extended from the barrel 3.

Referring again to FIGS. 3-5, one or more optional stops 34 may be positioned within the nipple 5 when a break-away valve 32 is attached to the valve 4. The stops 34 are nub-like elements or the like separately spaced about the port 20 so as to extend inward along the opening 21. The stops 34 are dimensioned so as to minimize interaction with fluid 37 traversing the nipple 5. However, the stops 34 are positioned and dimensioned so as to prevent the plug 35 and the stem 36 from completely traversing the port 20 after separation from the valve 4. This feature ensures proper function of the syringe 1 by preventing ejection of the plug 35 and the stem 36 from the syringe 1.

Referring again to FIGS. 3-5, an optional diaphragm 38 may be provided along the port 20 immediately adjacent to the valve 4. The diaphragm 38 could be a thin, flexible annular element which extends either from the port 20 so as to engage the plug 35 and/or the stem 36 or from the plug 35 and/or stem 36 so as to engage the port 20. The diaphragm 38 further seals the port 20 to insure the integrity of the fourth sealing interface 39, yet minimize obstructions that impede ejection of the fluid 37 from the syringe 1 when the fourth sealing interface 39 is open. In other embodiments, the diaphragm 38 may be a membrane-like element which covers the port 20 and prevents fluid from leaking through the nipple 5. In yet other embodiments, the diaphragm 38 may be a membrane or the like breakable via mechanical or pressure means to permit ejection of fluid from the second reservoir 15 during retraction of the plunger 2 into the barrel 3.

Referring again to FIGS. 3-5, the fourth sealing interface 39 may be beneficial when the syringe 1 does not include a cap or other means that support function of the valve 4. In preferred embodiments, the fourth sealing interface 39 is closed prior to and during extension of the plunger 2 from the barrel 3 to prevent the flow of gas 51 through the nipple 5 and open during retraction to permit ejection of the fluid 37 through the nipple 5. The fourth sealing interface 39 is closed when the plug 35 contacts the diaphragm 38 and open when the plug 35 is separated from the diaphragm 38.

Figure 6:
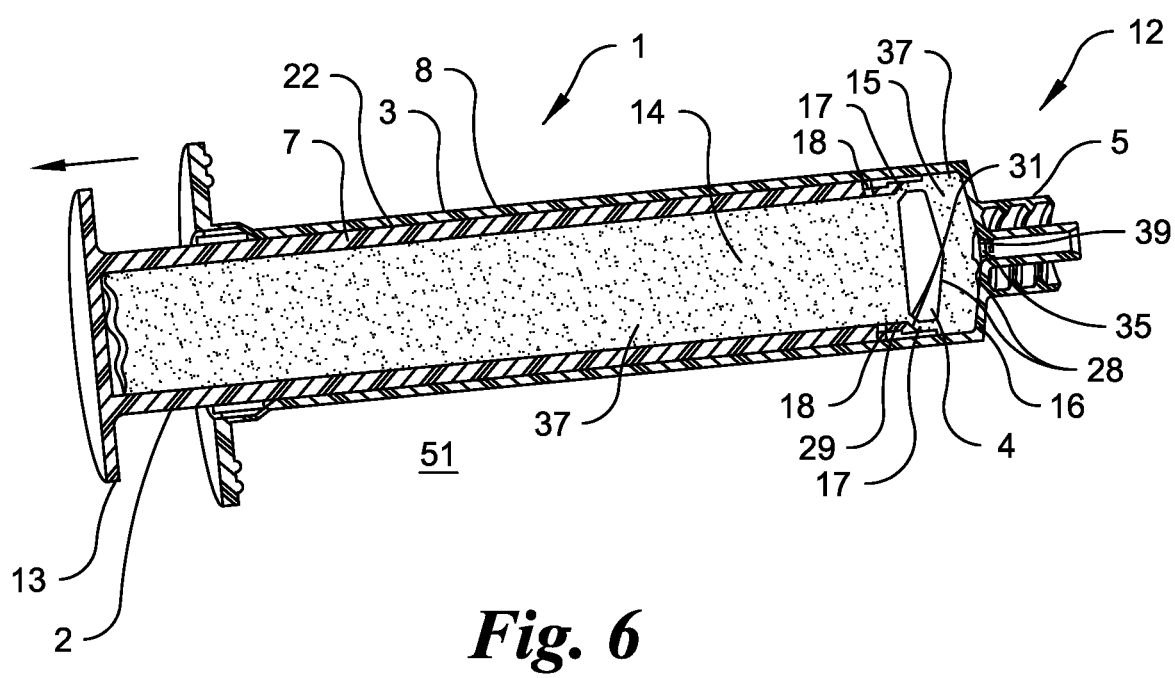
FIG. 6 is a perspective cross-section view illustrating flow of a fluid from a first reservoir through a valve into a second reservoir and location of an optional break-away valve after the valve is extended from the plunger and during extension of the plunger from a barrel of a telescoping syringe in accordance with an embodiment of the invention.

Referring now to FIG. 6, a syringe 1 is shown during extension of a plunger 2 from a barrel 3 whereby the side wall 7 along the plunger 2 moves toward the proximal end 13 and the side wall 8 along the barrel 3 remains fixed relative to the distal end 12. The plunger 2 is extended by pulling the plunger 2 away from the barrel 3 along the extension axis of the syringe 1. As the side wall 7 slides along the side wall 8, a lower pressure event is created between the plunger 2 and barrel 3 adjacent to the nipple 5 which temporarily fixes the valve 4 to the distal wall 16. After the valve 4 is fully extended from the side wall 8, the valve 4 then moves with the plunger 2 and away from the distal wall 16 thus providing the volume within the barrel 3 required to support the second reservoir 15. The result is an opening of the first, second, and third sealing interfaces 28, 29, and 31. The optional fourth sealing interface 39 remains closed. When the first sealing interface 28 is opened, either a cap along the nipple 5 or the plug 35 prevents a gas 51 from entering the nipple 5 thereby maintaining the pressure conditions required to transfer fluid 37 from the first reservoir 14 to the second reservoir 15. When the second sealing interface 29 is open, the gas 51 surrounding the syringe 1, one non-limiting example being air, is drawn into the gap 22 and then traverses the valve 4 via the inlets 18 into the first reservoir 14. When the third sealing interface 31 is open, the fluid 37 traverses the valve 4 via the outlets 17 and enters the expanding second reservoir 15.

Figure 7:
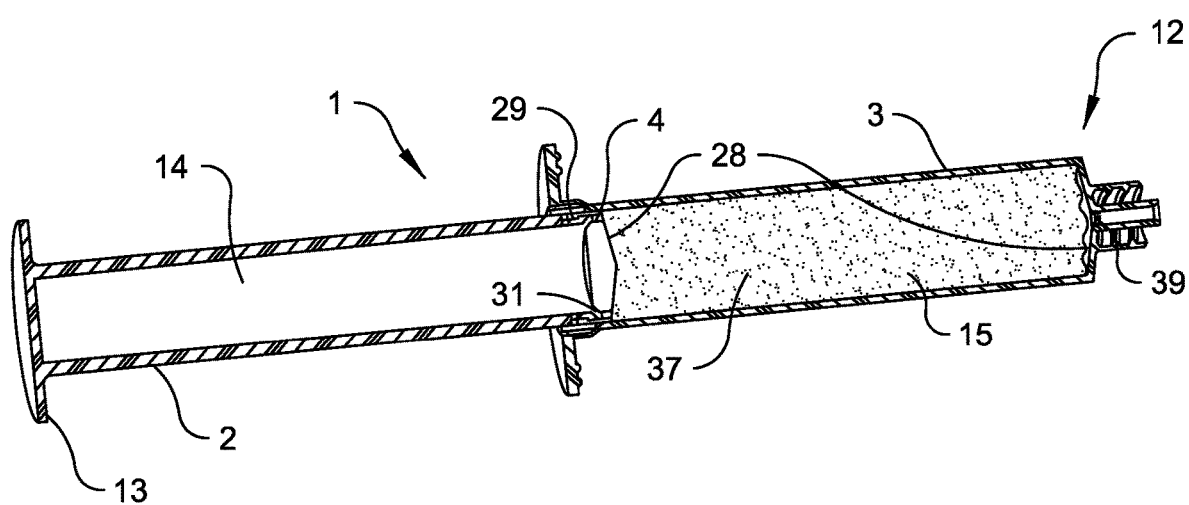
FIG. 7 is a perspective cross-section view illustrating a fluid within a second reservoir after transfer from a first reservoir via extension of a plunger from a barrel in accordance with an embodiment of the invention.

Referring now to FIG. 7, a syringe 1 is shown with the plunger 2 nearly fully extended from the barrel 3 and the fluid 37 originally residing within the first reservoir 14 now resides within the second reservoir 15. The valve 4 and corresponding first, second, and third sealing interfaces 28, 29, 31 remain open and the fourth sealing interface 39 remains closed until the plunger 2 is depressed from the direction of the proximate end 13 toward the distal end 12.

Figure 8:
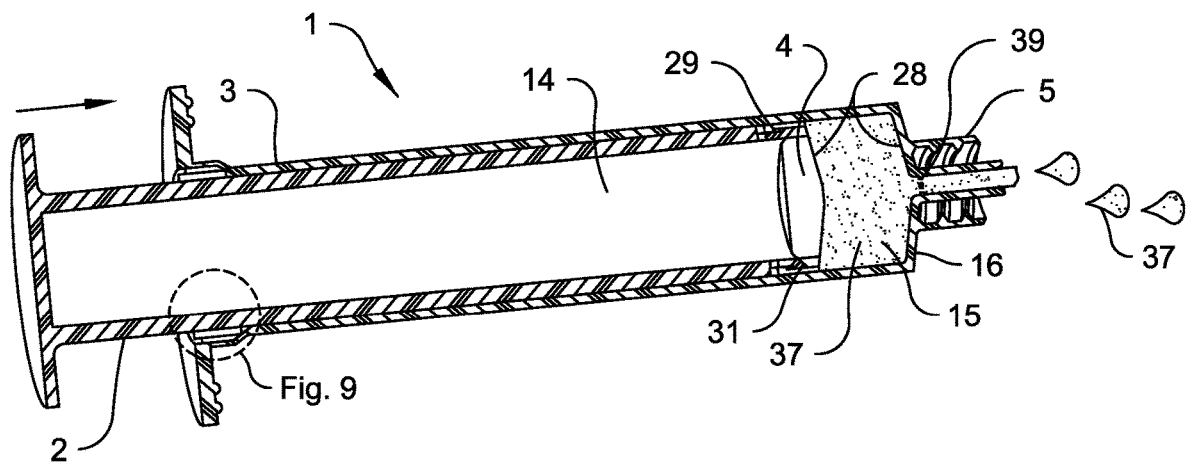
FIG. 8 is a perspective cross-section view illustrating ejection of a fluid from a second reservoir during retraction of a plunger into a barrel so that a valve along the plunger is closed and an optional break-away valve along the barrel is open in accordance with an embodiment of the invention.

Referring now to FIG. 8, a syringe 1 is shown nearly fully retracted so that the plunger 2 nearly completely contacts the distal wall 16 and the fluid 37 originating from the first reservoir 14 is now nearly completely ejected from the second reservoir 15. The plunger 2 is retracted by pushing the plunger 2 toward the barrel 3 along the extension axis of the syringe 1. The valve 4 and corresponding second and third sealing interfaces 29, 31 are closed to prevent the fluid 37 from reentering the first reservoir 14 and the optional fourth sealing interface 39 is open to permit the fluid 37 to traverse the nipple 5 prior to exiting the syringe 1. If the fourth sealing interface 39 is not provided, then a cap or the like (not shown) may be attached to the nipple 5 to ensure the pressure conditions required for transfer of the fluid 37 from the first reservoir 14 to the second reservoir 15. The cap is removed to permit ejection of the fluid 37 from the second reservoir 15.

Figure 9:
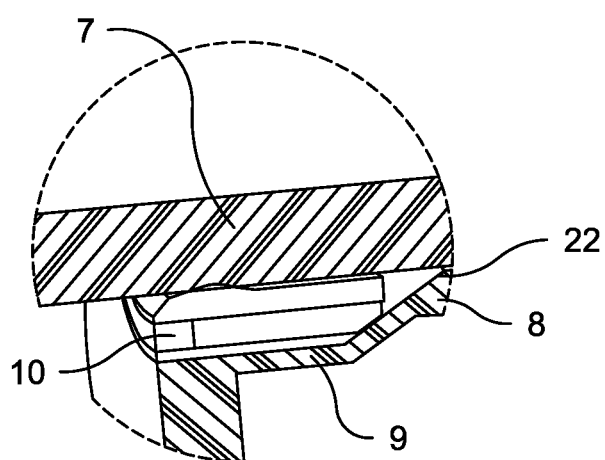
FIG. 9 is an enlarged cross-section view illustrating a filter element within a pocket between a plunger and a barrel whereby gas adjacent to a telescoping syringe must pass through the filter element prior to traversing a gap between the plunger and the barrel and thereafter entering a first reservoir as a fluid is transferred from a first reservoir to a second reservoir in accordance with an embodiment of the invention.
Figure 10:
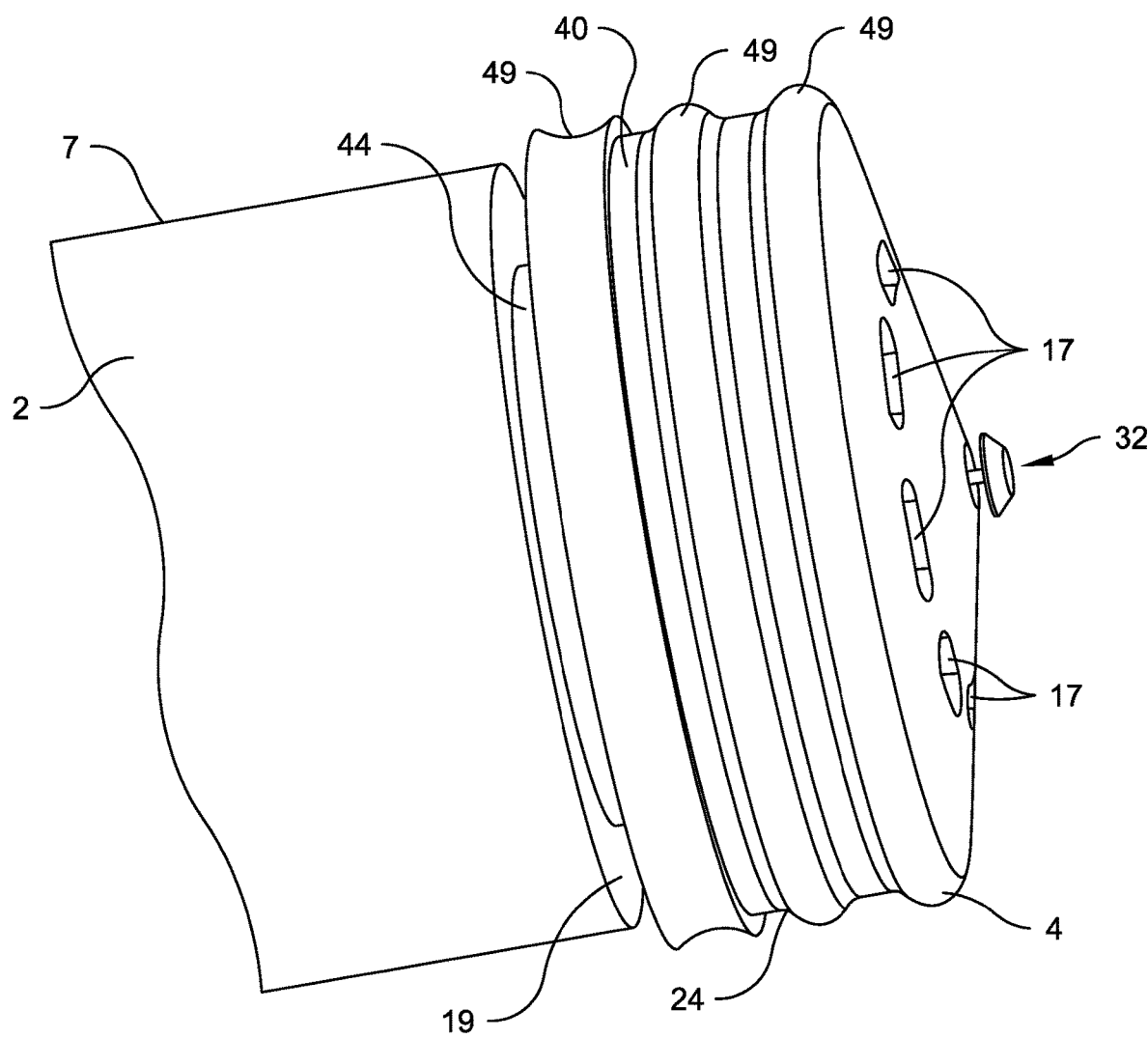
FIG. 10 is an enlarge perspective view illustrating a valve extendible from and retractable onto one end of a plunger whereby the valve is extended from the plunger, the valve includes at least one outlet, the plunger includes at least one optional inlet, concave and convex ridges are disposed along an outer surface of the valve, and an optional break-away valve is attached to the plunger in accordance with an embodiment of the invention.

Referring now to FIGS. 1 and 9, the syringe 1 may include an optional filter element 10 that removes particulates and other contaminants that could adversely interact or contaminate the fluid 37. In one possible embodiment, the filter element 10 could be a component, preferably annular shaped, housed within a pocket 9 disposed between the side walls 7, 8 adjacent to the gap 22. The pocket 9 may be a region whereby the gap 22 between side walls 7, 8 is larger than other portions of the same gap 22. The pocket 9 should support and secure the filter element 10 to the syringe 1, yet maintain sliding between the side walls 7, 8 and between the filter element 10 and one or both side walls 7, 8. The filter element 10 may be a mechanical filter, examples including but not limited to a charcoal-based filter or a HEPA filter.

Referring now to FIGS. 10-13, the valve 4 may include one or more ridges 49 that extend outward from the outer surface 40 along the annular extension 24. The ridges 49 may include convex or concave features which allow the valve 4 to contact the inner diameter of the barrel 3 so as to provide a slidable seal between the valve 4 and the barrel 3. The seal should be sufficient to maintain the pressure differential required between the first reservoir 14 and the second reservoir 15 to facilitate the fluid transfer described herein. Specifically, the first reservoir 14 should be at a higher pressure than the second reservoir 15 during extension of the syringe 1.

Referring again to FIGS. 11-13, the syringe 1 may include an optional biasing mechanism 48 that permits extension of the valve 4 from the plunger 2 during extension of the side wall 7 of the plunger 2 from the side wall 8 of the barrel 3 along the direction of the gap 22 and then thereafter permits retraction of the valve 4 onto the plunger 2. In some embodiments, retraction of the valve 4 by the biasing mechanism 48 may occur after some or all fluid 37 is transferred from the first reservoir 14 to the second reservoir 15. In other embodiments, retraction of the valve 4 by the biasing mechanism 48 may occur after the plunger 2 is either partially or completely extended from the barrel 3.

Referring again to FIGS. 10-13, the outer surface of the side wall 7 at the distal end 12 of the syringe 1 may include a proximal shoulder 19, an intermediate shoulder 43, and a distal shoulder 25. A first annular groove 44 is interposed between and bounded by the proximal shoulder 19 and the intermediate shoulder 43. A second annular groove 45 is interposed between and bounded by the intermediate shoulder 43 and the distal shoulder 25. The inner surface of the annular extension 24 may include an annular flange 41 and an elastic annular flange 42. A first inner annular groove 46 is interposed between and bound by the annular flange 41 and the elastic annular flange 42. A second inner annular groove 47 is interposed between and bounded by the elastic annular flange 42 and the barrier 23. The outer surface of the side wall 7 and the inner surface of the annular extension 24 are positioned so that the annular flange 41 extends into the annular groove 44, the intermediate shoulder 43 extends into the first inner annular groove 46, the elastic annular flange 42 extends into the second annular groove 45, and the distal shoulder 25 extends into the second inner annular groove 47.

Referring again to FIGS. 11-13, the annular flange 41 slides along the first annular groove 44 so as to cover the inlets 18 when the annular flange 41 is biased toward the proximal shoulder 19 and uncover the inlets 18 when the annular flange 41 is biased toward the intermediate shoulder 43. In preferred embodiments, the elastic annular flange 42 contacts the distal shoulder 25 when the annular flange 41 is biased toward the proximal shoulder 19. This arrangement requires the elastic annular flange 42 to deform as the annular flange 41 moves with the valve 4 in the direction of the intermediate shoulder 43, as represented by the shapes for the elastic annular flange 42 in FIG. 11 versus FIGS. 12 and 13. Deformation of the elastic annular flange 42 ceases when the annular flange 41 contacts the intermediate shoulder 43. The width of the first annular groove 44 should permit the annular flange 41 to move between the proximal shoulder 19 and the intermediate should 43. The width of the first inner annular groove 46 should permit the intermediate shoulder 43 to move between the annual flange 41 and the elastic annular flange 42. The width of the second inner annular groove 47 should allow the distal shoulder 25 to contact both the elastic annular flange 42 and the barrier 23.

The biasing mechanism 48 is deformable and resilient. In preferred embodiments, the elastic annular flange 42 is deformable in that it changes shape as the elastic annular flange 42 moves into and interacts with the distal shoulder 25 when the valve 4 is extended from the plunger 2 during extension of the plunger 2 from the barrel 3. The elastic annular flange 42 is resilient in that it recovers at least most of its original shape sometime after the extension of the plunger 2 from the barrel 3. The recovery process may occur with or without input by or assistance from the user. The spring-like functionality of the elastic annular flange 42 causes the valve 4 to retract onto the plunger 2 so that the annular flange 41 is once again biased toward the proximal shoulder 19 and the inlets 18 and outlets 17 are once again closed. While specific reference is made to a mechanism wherein a flange is deformable and resilient other mechanisms capable of spring or spring-like functionality are likewise applicable to embodiments of the invention.

Referring again to FIG. 11, the valve 4 is seated onto the plunger 2 before extension of the plunger 2 from the barrel 3 so that the elastic annular flange 42 contacts and interacts with the distal shoulder 25 with no or limited deformation to the elastic annular flange 42. The position of the valve 4 with respect to the plunger 2 and the barrel 3 ensures that the barrier 23 contacts the distal end 16 of the barrel 3 so that the first sealing interface 28 is closed, the annular flange 41 contacts the proximal shoulder 19 and overlays the inlets 18 so that the second sealing interface 29 is closed, and the circumferential end 30 contacts the valve 4 and overlays the outlets 17 so that the third sealing interface 31 is closed.

Referring again to FIG. 12, the valve 4 is extended from the plunger 2 and the plunger 2 is equally extended from the barrel 3 so that the elastic annular flange 42 contacts and interacts with the distal shoulder 25 and the elastic annular flange 42 is deformed by the interaction. The position of the valve 4 with respect to the plunger 2 and the barrel 3 ensures that the barrier 23 contacts the distal end 16 of the barrel 3 so that the first sealing interface 28 remains closed, the annular flange 41 contacts the intermediate shoulder 43 and no longer overlays the inlets 18 so that the second sealing interface 29 is open, and the circumferential end 30 is separated from the valve 4 and no longer overlays the outlets 17 so that the third sealing interface 31 is open.

Referring again to FIG. 13, the plunger 2 is now more extended from the barrel 3 than the valve 4 is extended from the plunger 2 so that the elastic annular flange 42 remains deformed by the interaction with the distal shoulder 25. The position of the valve 4 with respect to the plunger 2 and the barrel 3 ensures that the barrier 23 no longer contacts the distal end 16 of the barrel 3 so that the first sealing interface 28 is now open, the annular flange 41 contacts the intermediate shoulder 43 and no longer overlays the inlets 18 so that the second sealing interface 29 is open, and the circumferential end 30 is separated from the valve 4 and no longer overlays the outlets 17 so that the third sealing interface 31 is open. A portion of the fluid 37 from the first reservoir 14 now resides within the second reservoir 15.

Figure 11:
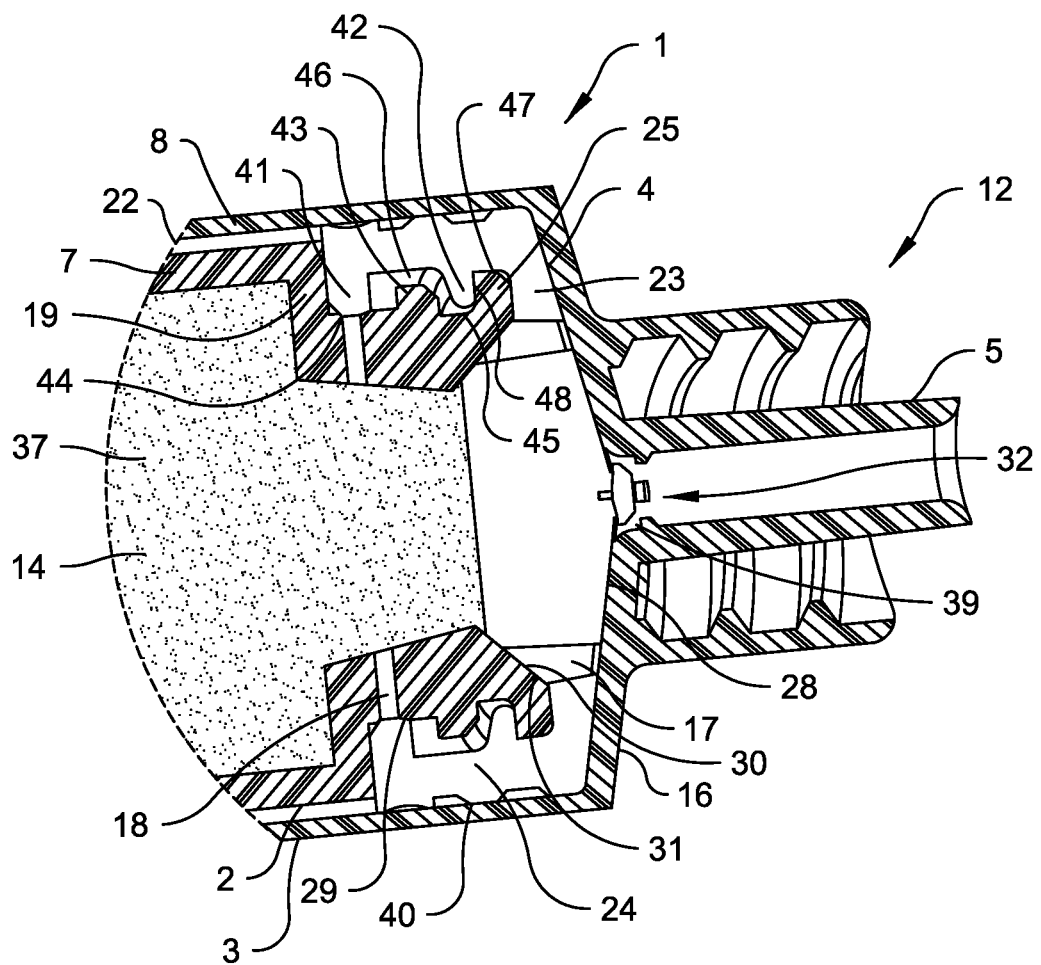
FIG. 11 is an enlarged cross-section view illustrating a valve with a biasing mechanism prior to extension of a plunger from a barrel whereby the valve is disposed in a closed configuration which prevents a fluid from exiting a first reservoir within the plunger in accordance with an embodiment of the invention.

The mechanical energy stored in the valve 4 due to deformation of the elastic annular flange 42 permits the elastic annular flange 42 to recover at least most of its original shape so that the valve 4 returns to its original position relative to the plunger 2 such as in FIG. 11. When this event occurs, however, it is often preferred that at least a majority of the fluid 37 from the first reservoir 14 now resides within the second reservoir 15.

Referring now to FIGS. 14a-14c, one or more inlets 18 in some embodiments may be positioned along the proximal shoulder 19 whereby the second sealing interface 29 is formed at contact between the valve 4 and the outer surface of the proximal shoulder 19. In some embodiments, the second sealing interface 29 may include the surface of the side wall 7 as shown by way of example in FIG. 3 or 11. An optional biasing mechanism 48 may permit extension of the valve 4 from the plunger 2 during extension of the side wall 7 of the plunger 2 from the side wall 8 of the barrel 3 and retraction of the valve 4 onto the plunger 2 after extension between the side walls 7, 8 is completed. In some embodiments, retraction of the valve 4 by the biasing mechanism 48 may occur after some or all fluid 37 is transferred from the first reservoir 14 to the second reservoir 15. In other embodiments, retraction of the valve 4 by the biasing mechanism 48 may occur after the plunger 2 is either partially or completely extended from the barrel 3.

Referring again to FIGS. 14a-14c, the outer surface of the side wall 7 at the distal end 12 of the syringe 1 includes the proximal shoulder 19, an intermediate shoulder 43, and a distal shoulder 25. A first annular groove 44 is interposed between and bounded by the proximal shoulder 19 and the intermediate shoulder 43. A second annular groove 45 is interposed between and bounded by the intermediate shoulder 43 and the distal shoulder 25. The inner surface of the annular extension 24 may include an annular flange 41 and an elastic annular flange 42. A first inner annular groove 46 is interposed between and bound by the annular flange 41 and the elastic annular flange 42. A second inner annular groove 47 is interposed between and bounded by the elastic annular flange 42 and the barrier 23. The outer surface of the side wall 7 and the inner surface of the annular extension 24 are positioned so that the annular flange 41 extends into the annular groove 44, the intermediate shoulder 43 extends into the first inner annular groove 46, the elastic annular flange 42 extends into the second annular groove 45, and the distal shoulder 25 extends into the second inner annular groove 47.

Referring again to FIGS. 14a-14c, the annular flange 41 slides along the first annular groove 44 so as to cover the inlets 18 along the proximal shoulder 19 when the annular flange 41 is biased toward the proximal shoulder 19 and uncover the inlets 18 along the proximal shoulder 19 when the annular flange 41 is biased toward the intermediate shoulder 43. In preferred embodiments, the elastic annular flange 42 contacts the distal shoulder 25 when the annular flange 41 is biased toward the proximal shoulder 19. The elastic annular flange 42 deforms as the annular flange 41 moves with the valve 4 in the direction of the intermediate shoulder 43, as represented by the change in shape of the elastic annular flange 42 from FIG. 14b to FIG. 14c. Deformation of the elastic annular flange 42 ceases when the annular flange 41 contacts the intermediate shoulder 43. In some preferred embodiments, the width of the first annular groove 44 should permit the annular flange 41 to move between the proximal shoulder 19 and the intermediate should 43. In other preferred embodiments, the width of the first inner annular groove 46 should permit the intermediate shoulder 43 to move between the annual flange 41 and the elastic annular flange 42. In yet other preferred embodiments, the width of the second inner annular groove 47 should allow the distal shoulder 25 to contact both the elastic annular flange 42 and the barrier 23.

Referring again to FIGS. 14b and 14c, the biasing mechanism 48 is deformable and resilient. In preferred embodiments, the elastic annular flange 42 is deformable in that it changes shape as the elastic annular flange 42 moves into and interacts with the distal shoulder 25 when the valve 4 is extended from the plunger 2 during extension of the plunger 2 from the barrel 3. The elastic annular flange 42 is resilient in that it recovers at least most of its original shape sometime after the extension of the plunger 2 from the barrel 3. The recovery process may occur with or without input by or assistance from the user. The spring-like functionality of the elastic annular flange 42 causes the valve 4 to retract onto the plunger 2 so that the annular flange 41 is once again biased toward the proximal shoulder 19 and both inlets 18 and outlets 17 are once again closed. While specific reference is made to a mechanism wherein a flange is deformable and resilient other mechanisms capable of spring or spring-like functionality are likewise applicable to embodiments of the invention.

Referring again to FIG. 14b, the valve 4 is seated onto the plunger 2 in a first position before extension of the plunger 2 from the barrel 3. The elastic annular flange 42 may contact and interact with the distal shoulder 25 with no or limited deformation to the elastic annular flange 42. The position of the valve 4 with respect to the plunger 2 and the barrel 3 allows the barrier 23 to contact the distal end 16 of the barrel 3 so that the first sealing interface 28 is closed, the annular flange 41 contacts the proximal shoulder 19 and overlays the inlets 18 so that the second sealing interface 29 along the proximal shoulder 19 is closed, and the circumferential end 30 of the side wall 7 contacts the barrier 23 and overlays the outlets 17 so that the third sealing interface 31 is closed, the latter also further illustrated in FIG. 3.

Referring again to FIG. 14c, the valve 4 is extended from the plunger 2 and the plunger 2 is extended from the barrel 3 from the first position to a second position so that the elastic annular flange 42 contacts and interacts with the distal shoulder 25 causing the elastic annular flange 42 to deform. The position of the valve 4 with respect to the plunger 2 and the barrel 3 ensures that the barrier 23 contacts the distal end 16 of the barrel 3 so that the first sealing interface 28 remains closed at least initially, the annular flange 41 contacts the intermediate shoulder 43 and no longer overlays the inlets 18 so that the second sealing interface 29 is open, and the circumferential end 30 of the side wall 7 is separated from the valve 4 and no longer overlays the outlets 17 so that the third sealing interface 31 is open. When the second sealing interface 29 is open, a gas may pass between the annular flange 41 and the proximal shoulder 19 and then enter the inlet(s) 18. The inlet(s) 18 may be substantially circular shaped and/or elongated, such as illustrated in FIG. 14a. The gas may traverse the gap 22 between the side walls 7, 8 before entering the inlets 18.

Referring again to FIGS. 14a-14c, the annular flange 41 slidingly engages the annular groove 44 between first and second positions. In preferred embodiments, the first position corresponds to the second sealing interface 29 and the third sealing interface 31 being closed so that the inlets 18 and outlets 17 are closed. In preferred embodiments, the second position corresponds to the second sealing interface 29 and the third sealing interface 31 being open so that the inlets 18 and outlets 17 are open. In some embodiments, the inlets 18 and the outlets 17 may be open for at least a portion of the distance between the first and second positions. In other preferred embodiments, the second position corresponds to the extendible limit of the valve 4 from the plunger 2. The annular flange 41 may or may not contact the intermediate shoulder 43 at the second position. In some embodiments, the second position may be defined in part or whole by the extendible movement by the valve 4 as permitted by the elastic annular flange 42. In other embodiments, the second position may be defined in part or whole by either direct or indirect interaction between one or more features of the valve 4 and the plunger 2. Regardless, the inlets 18 and the outlets 17 are understood to be open when the valve is not in the first position. The inlets 18 may be disposed along the proximal shoulder 19 or the side wall 7, the latter illustrated by way of example in FIGS. 2 and 11.

Referring again to FIG. 14c, the elastic annular flange 42 remains deformed by the interaction with the distal shoulder 25 as the plunger 2 is extended from the barrel 3. By way of example in FIG. 13, the position of the valve 4 with respect to the plunger 2 and the barrel 3 ensures that the barrier 23 no longer contacts the distal end 16 of the barrel 3 so that the first sealing interface 28 is now open, the annular flange 41 contacts the intermediate shoulder 43 and no longer overlays the proximal shoulder 19 and the inlets 18 thereon (see FIG. 14c) so that the second sealing interface 29 is open, and the circumferential end 30 of the side wall 7 is separated from the valve 4 and no longer overlays the outlets 17 so that the third sealing interface 31 is open. A portion of the fluid 37 from the first reservoir 14 now resides within the second reservoir 15. The mechanical energy stored in the valve 4 due to deformation of the elastic annular flange 42 permits the elastic annular flange 42 to recover at least most of its original shape so that the valve 4 returns to its original position relative to the plunger 2 such as in FIG. 14b. When this event occurs, however, it is often preferred that at least a majority of the fluid 37 from the first reservoir 14 now resides within the second reservoir 15. The fluid 37 residing within the second reservoir 15 is ejected from the syringe 1 by retracting the plunger 2 into the barrel 3.

Figure 12:
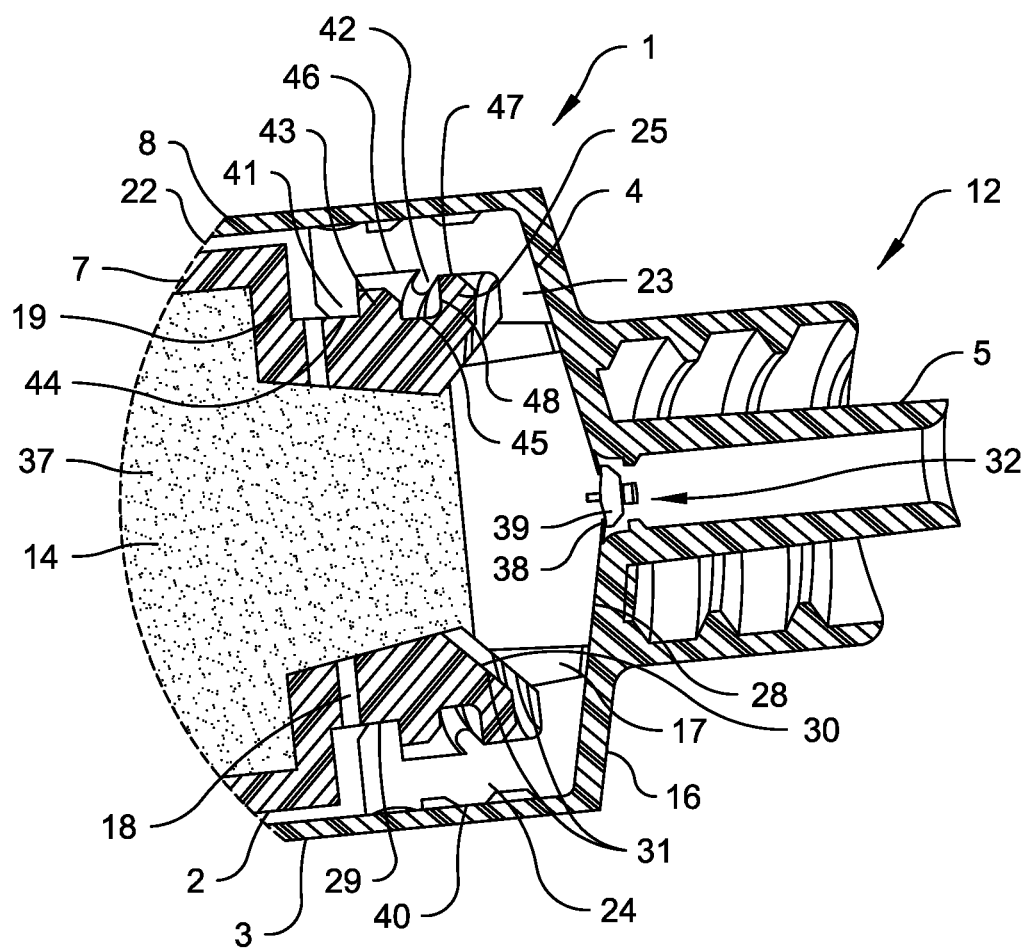
FIG. 12 is an enlarged cross-section view illustrating a valve with a biasing mechanism after initial extension of a plunger from a barrel whereby the valve is disposed in an open configuration to permit gas to enter a first reservoir and to permit transfer of a fluid from the first reservoir within the plunger to a second reservoir within the barrel in accordance with an embodiment of the invention.
Figure 13:
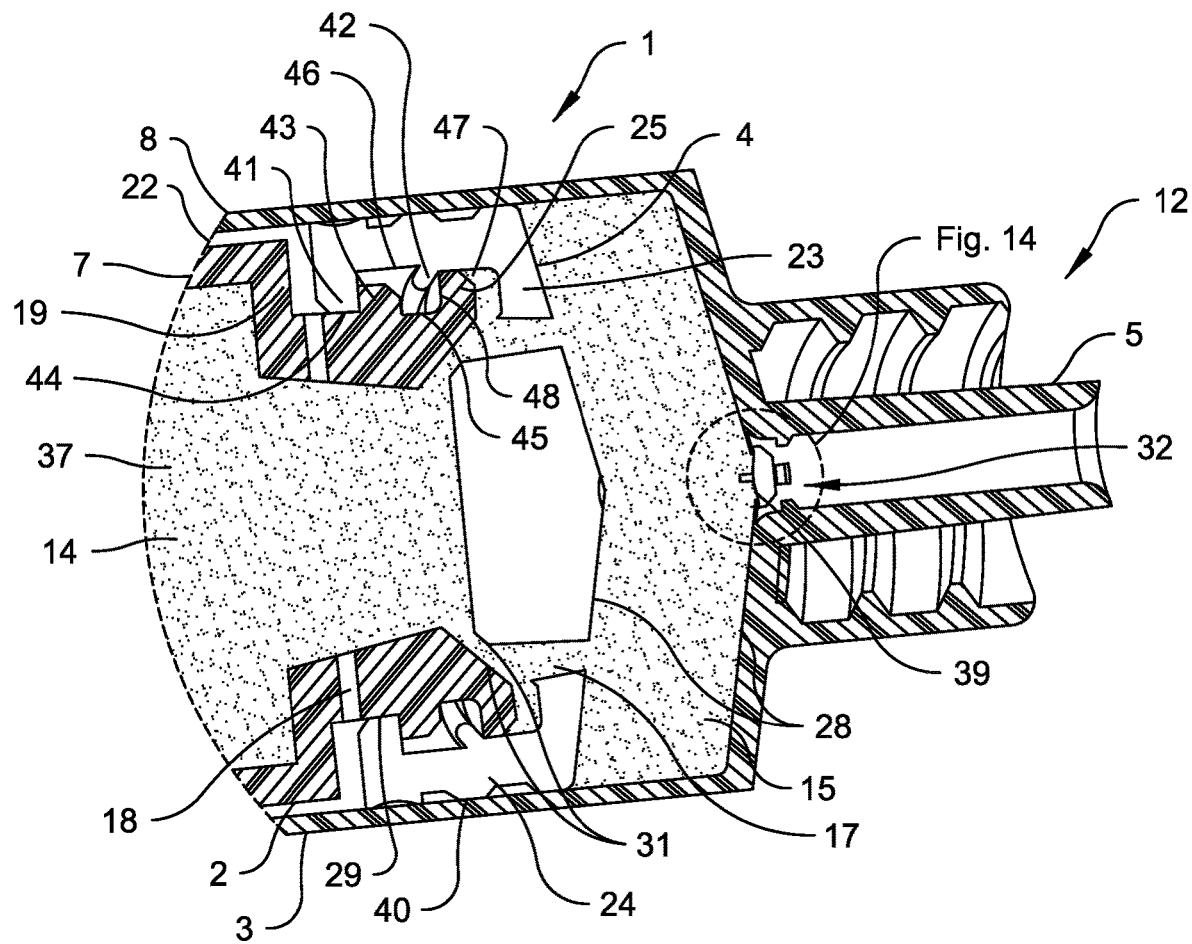
FIG. 13 is an enlarged cross-section view illustrating a valve with a biasing mechanism during extension of a plunger from a barrel whereby the valve is disposed in an open configuration permitting transfer of a fluid from a first reservoir within the plunger to a second reservoir within the barrel and further permitting replacement of fluid exiting the first reservoir by gas drawn into the syringe during extension in accordance with an embodiment of the invention.
Figure 15A:
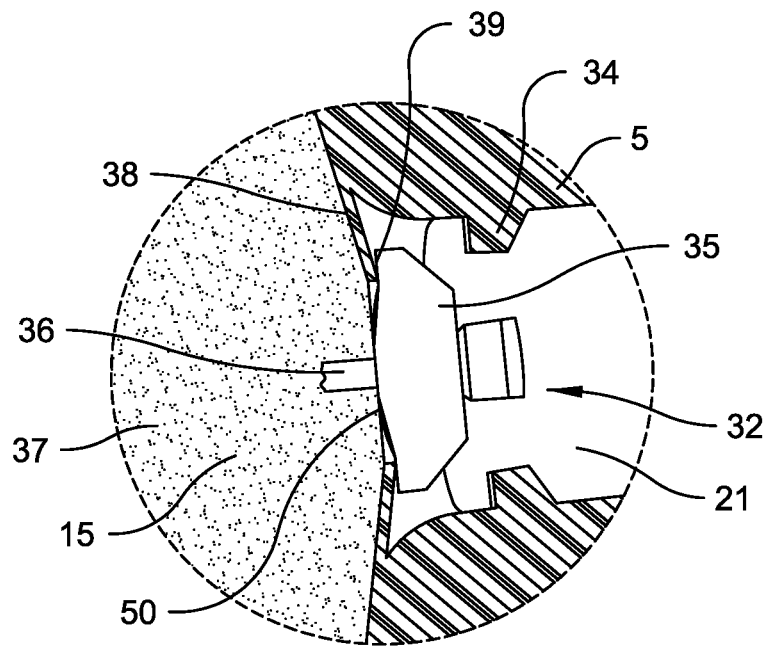
FIG. 15a is an enlarged cross-section view illustrating a break-away valve after separation from a one-way fluid/gas transfer valve and prior to retraction of a plunger into a barrel whereby a plug within the break-away valve provides a seal that prevents gas from entering the syringe via a nipple in accordance with an embodiment of the invention.

Referring now to FIGS. 12, 13 and 15a, a fourth sealing interface 39 may be provided by a break-away valve 32 and a diaphragm 38 facilitating ejection of fluid 37 from the syringe 1 when the fourth sealing interface 39 is open and preventing or limiting ejection of fluid 37 from the syringe 1 when the fourth sealing interface 39 is closed. The diaphragm 38 may be attached to the barrel 3 adjacent to the intersection between barrel 3 and the nipple 5. The fourth sealing interface 39 may be closed when a plug 32 and a stem 36 are attached to or separated from the valve 4, the former represented in FIGS. 12 and 13 and the latter represented in FIG. 15a, so that the stem 36 resides within an opening 50 through the diaphragm 38 and the plug 32 physically contacts the diaphragm 38. The fourth sealing interface 39 is closed during extension of the plunger 2 from the barrel 3 to prevent ejection of fluid 37 from the second reservoir 15.

Figure 15B:
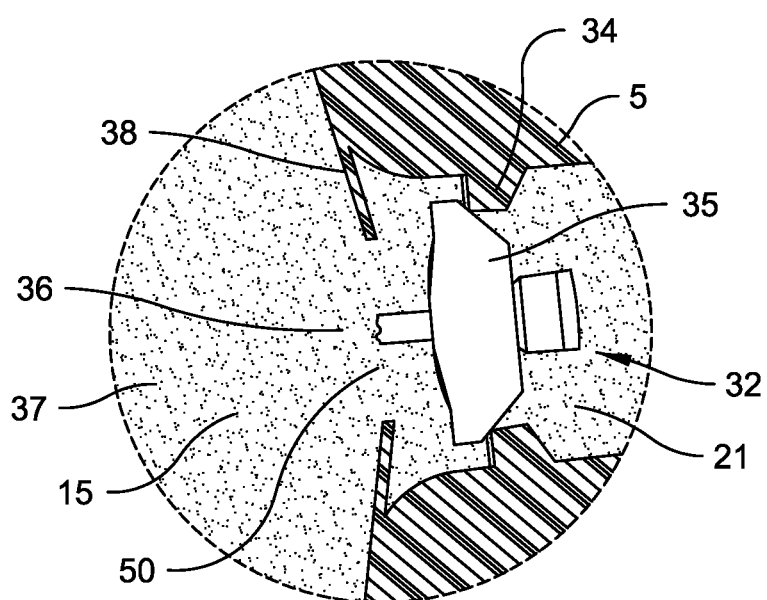
FIG. 15b is an enlarged cross-section view illustrating a break-away valve after separation from a one-way fluid/gas transfer valve and during retraction of a plunger into a barrel whereby a plug within the break-away valve is positioned within a nipple to facilitate ejection of a fluid from a syringe via the nipple in accordance with an embodiment of the invention.

Referring now to FIGS. 12, 13 and 15b, the fourth sealing interface 39 is open during retraction of the plunger 2 into the barrel 3 causing fluid 37 to flow out of the second reservoir 15 into and through the nipple 5. The resultant flow field unseats the plug 35 and the stem 36 from the diaphragm 38 causing both to move into the nipple 5. In many applications, it may be undesirable for the plug 35 and the stem 36 to remain contained within the syringe 1. One or more mechanical stops 34 may be provided along the inside surface of the nipple 5 adjacent to the diaphragm 38 in order to arrest the plug 35 and the stem 36 within the nipple 5. The opening 50 along the diaphragm 38 and the interaction between the plug 35 and the stop(s) 34 should allow the desired flow rate(s) of fluid 37 from the syringe 1.

Figure 16A:
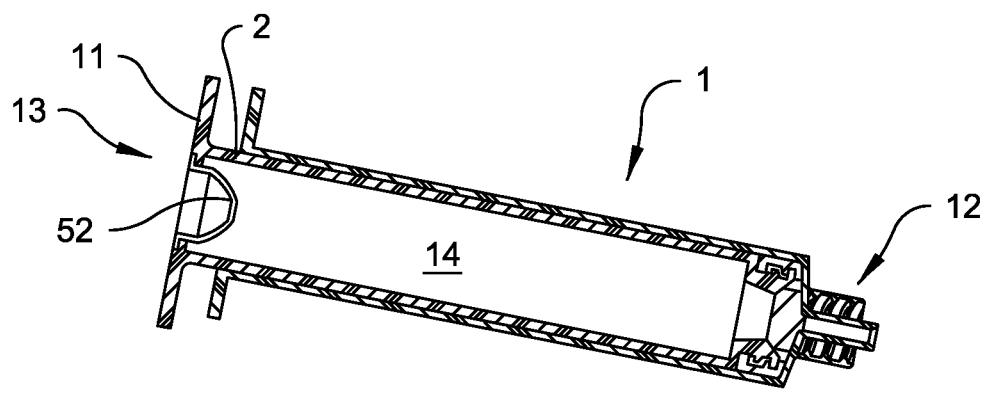
FIG. 16a is a cross-section view illustrating an optional inlet provided along a proximal wall of a plunger thereby permitting a gas to directly enter a first reservoir within the plunger as fluid exits the plunger in accordance with an embodiment of the invention.
Figure 16B:
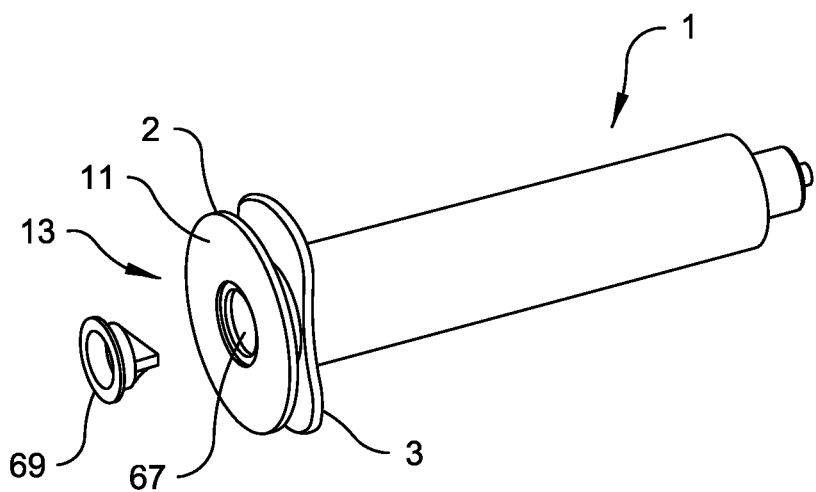
FIG. 16b is a partial exploded view illustrating the optional inlet as a check valve secured within an opening along the proximal wall of the plunger in accordance with an embodiment of the invention.

Referring now to FIGS. 16a and 16b, it may be advantageous to provide an inlet 52 at the proximal end 13 of the syringe 1 either in addition to or in place of the inlet(s) 18. The inlet 52 could be comprised of a check valve 69 or the like secured within an opening 67 along the proximal wall 11. In preferred embodiments, the check valve 69 is situated so as to directly communicate with the first reservoir 14. The check valve 69 is understood to be a device which otherwise facilitates proper function of the syringe 1. By way of example, the check valve 69 could permit gas to enter the plunger 2 as fluid is transferred from the plunger 2 to the barrel 3 and could also prevent gas from exiting the plunger 2 and fluid from reentering the plunger 2 as fluid is expelled from the syringe 1 at the distal end 12.

Figure 17A:
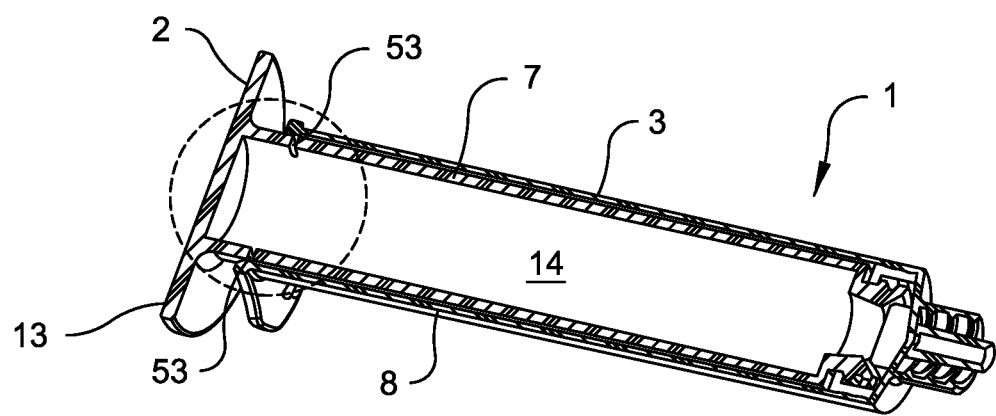
FIG. 17a is a cross-section view illustrating a pair of optional inlets adjacent to a proximal end of a plunger for a telescoping syringe in accordance with an embodiment of the invention.

Referring now to FIG. 17a, it may be advantageous to provide one or more inlets 53 along the side wall 7 of the plunger 2 either in addition to or in place of the inlet(s) 18. An inlet 53 is understood to be an opening which permits proper function of the syringe 1 whereby gas is permitted to flow into the first reservoir 14 as fluid is transferred from the plunger 2 to the barrel 3. In preferred embodiments, the inlets 53 may be situated adjacent to the proximal end 13 of the syringe 1.

Figure 17B:
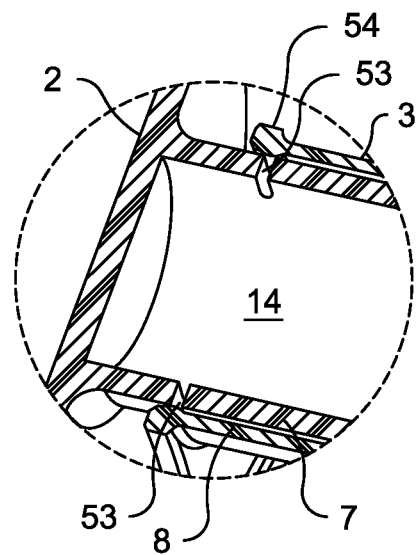
FIG. 17b is an enlarged cross-section view illustrating contact between the pair of optional inlets along the plunger and an annular sealing ring along a barrel when the plunger is fully retracted into the barrel in accordance with an embodiment of the invention.
Figure 17C:
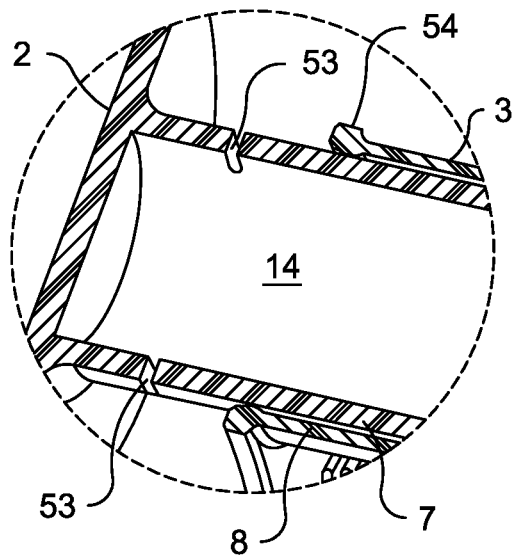
FIG. 17c is an enlarged cross-section view illustrating separation between the pair of optional inlets along the plunger and the annular sealing ring along the barrel when the plunger is extended from the barrel thereby permitting a gas to fill a first reservoir within the plunger as fluid exits the plunger in accordance with an embodiment of the invention.

Referring now to FIGS. 17a, 17b, and 17c, the side wall 8 of the barrel 3 may include an annular sealing ring 54 which engages the outer surface of the side wall 7 along the plunger 2. As illustrated in FIG. 17b, the annular sealing ring 54 is preferred to be situated to sealing engage the inlet(s) 53 when the plunger 2 is retracted into the barrel 3 so as to prevent fluid from exiting the first reservoir 14 prior to or after use of the syringe 1. As illustrated in FIG. 17c, the annular sealing ring 54 is likewise preferred to sealingly disengage from the inlet(s) 53 when the plunger 2 is extended from the barrel 3 so as to permit gas to enter the first reservoir 14 as fluid flows from the plunger 2 to the barrel 3.

The annular sealing ring 54 is understood to be a feature(s) and/or an element(s) that facilitates closure and sealing of the inlet(s) 53 when the annular sealing 54 overlays the inlet(s) 53. By way of example only, the annular sealing ring 54 may be a protrusion facilitating an interference fit over a portion of the outer surface along the side wall 8 contacted by the protrusion, as illustrated in FIGS. 17b and 17c. The protrusion may be molded or formed onto the side wall 7 or otherwise secured to the side wall 7. The protrusion may be composed of the same or a different material(s) comprising the side wall 7.

Referring now to FIGS. 18a and 18b, it may be advantageous to separate the location where gas enters the plunger 2 and the location where gas enters the first reservoir 14, either in addition to or in place of the inlet(s) 18. In one example, a gas could enter the passageway 55 at a first end 56 biased toward the distal end 12 of a syringe 1 and enter the first reservoir 14 at a second end 57 via at least one inlet 58 biased toward the proximal end 13. The passageway 55 traverses and passes through the side wall 7 of the plunger 2 between the proximal shoulder 19 oriented toward the distal end 12 and at least one inlet(s) 58 adjacent to the proximal end 13.

Figure 18C:
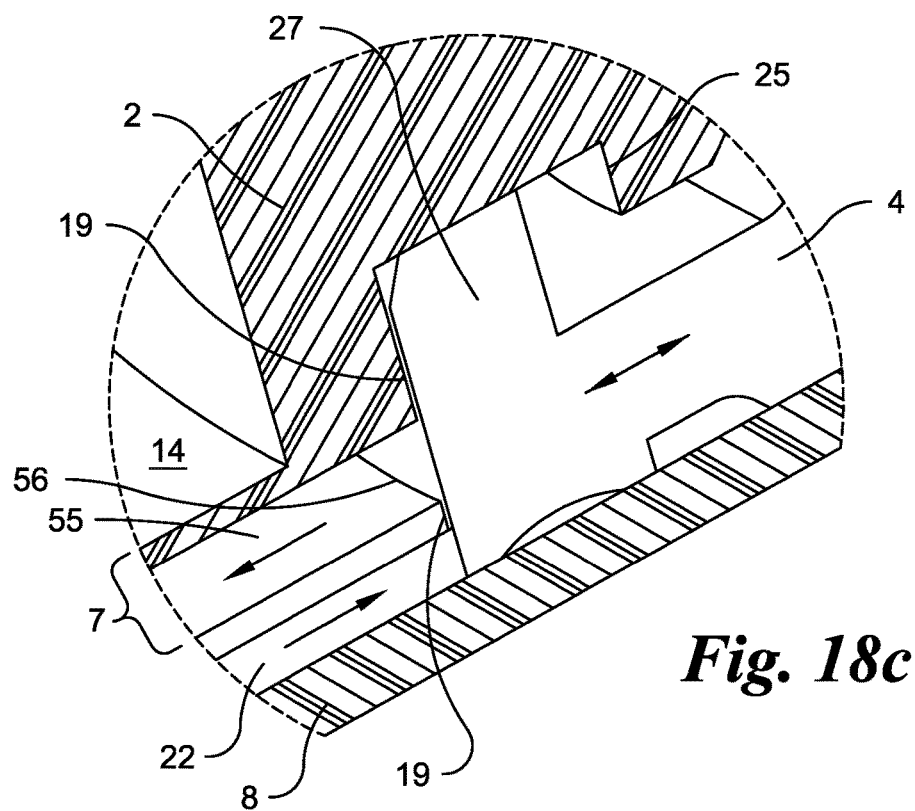
FIG. 18c is an enlarged section view illustrating arrangement of the passageway with respect to a gap between the side wall of the plunger and a side wall of a barrel adjacent to a valve at the distal end of the plunger in accordance with an embodiment of the invention.

Referring now to FIGS. 18*b* and 18*c*, the passageway 55 provides an opening at the proximal shoulder 19. In preferred embodiments, the passageway 55 bifurcates a portion of the side wall 7 so as to form a pathway through the side wall 7. The first end 56 of the passageway 55 engages the valve 4 at the proximal shoulder 19. The passageway 55 is closed when the annular flange 27 contacts the proximal shoulder 19 thereby preventing gas from passing into the passageway 55 at the first end 56. The passageway 55 is open when the annular flange 27 is biased away from the proximal shoulder 19 in the direction of the distal shoulder 25 thereby allowing gas to pass into the passageway 55 at the first end 56.

Figure 18D:
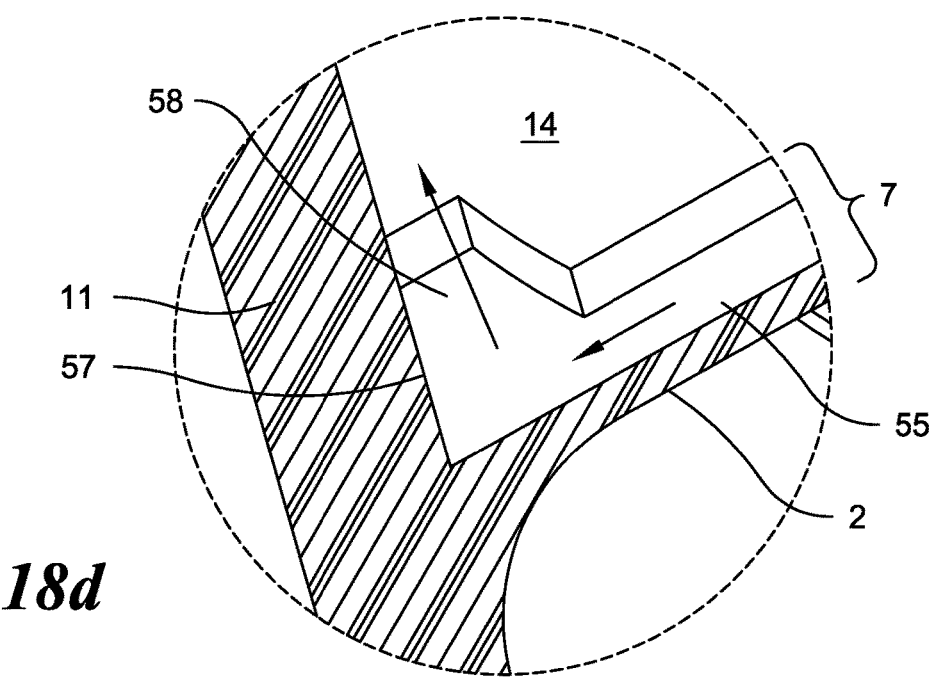
FIG. 18d is an enlarged section view illustrating arrangement of the passageway with respect to an optional inlet which permits the gas to enter the first reservoir when the plunger is extended from the barrel and the valve at the distal end of the plunger is in the open position in accordance with an embodiment of the invention.

Referring now to FIGS. 18*b*, 18*c*, and 18*d*, a gap 22 is interposed between the side wall 7 of the plunger 2 and the side wall 8 of the barrel 3 adjacent to the passageway 55. The inlet 58 cooperates with the passageway 55 and the gap 22 to permit proper function of the syringe 1.

Referring again to FIGS. 18*b*, 18*c*, and 18*d*, the passageway 55 is communicable with the gap 22 when the annular flange 27 is biased away from the proximal shoulder 19 thereby allowing gas to enter the passageway 55 from the gap 22. In this configuration, the plunger 2 is extended from the barrel 3, the valve 4 is biased away from the proximal shoulder 19 so that a vacuum is formed within the first reservoir 14 as fluid is transferred from the first reservoir 14 into the barrel 3, gas flows into the gap 22 in the direction of the distal end 12 in response to the vacuum, gas is redirected at the first end 56 into the passageway 55, gas flows into the passageway 55 in the direction of the proximal end 13, and gas is redirected at a second end 57 into the first reservoir 14 via the inlet 58 adjacent to the proximal wall 11.

Referring again to FIGS. 18*b*, 18*c*, and 18*d*, the passageway 55 is sealed from the gap 22 when the annular flange 27 contacts the proximal shoulder 19 thereby preventing gas from entering the passageway 55 from the direction of the gap 22. In this configuration, fluid within the plunger 2 is prevented from leaking from the first reservoir 14 prior to transfer to the barrel 3, gas is prevented from leaking out of the first reservoir 14 after fluid is transferred from the plunger 2 to the barrel 3, and fluid is prevented from re-entering the first reservoir 14 after transferred from the plunger 2 to the barrel 3.

Figure 19A:
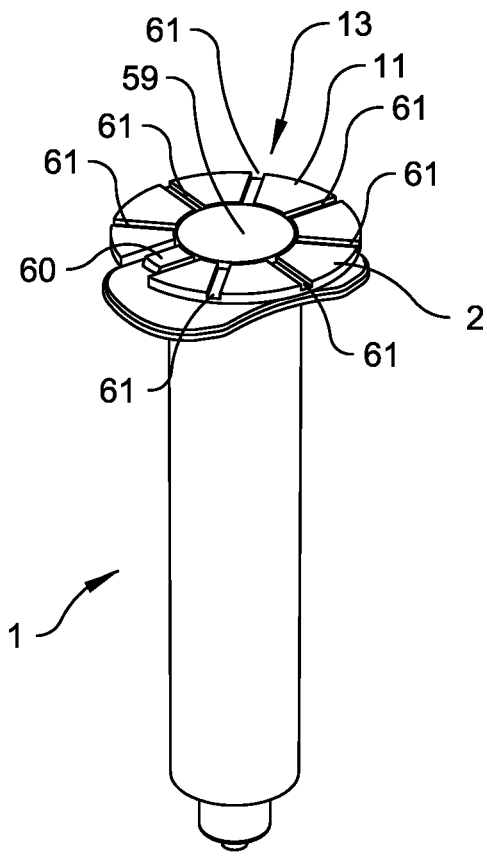
FIG. 19a is a perspective view illustrating a cap operable to form an optional inlet disposed at a proximal wall of a plunger at one end of a telescoping syringe in accordance with an embodiment of the invention.
Figure 19B:
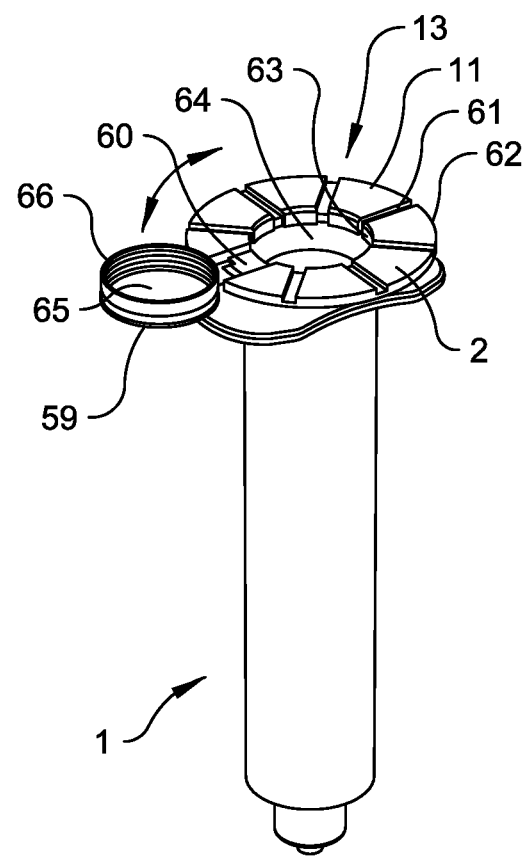
FIG. 19b is a perspective view illustrating the cap hingedly attached to the proximal wall of the plunger in accordance with an embodiment of the invention.
Figure 19C:
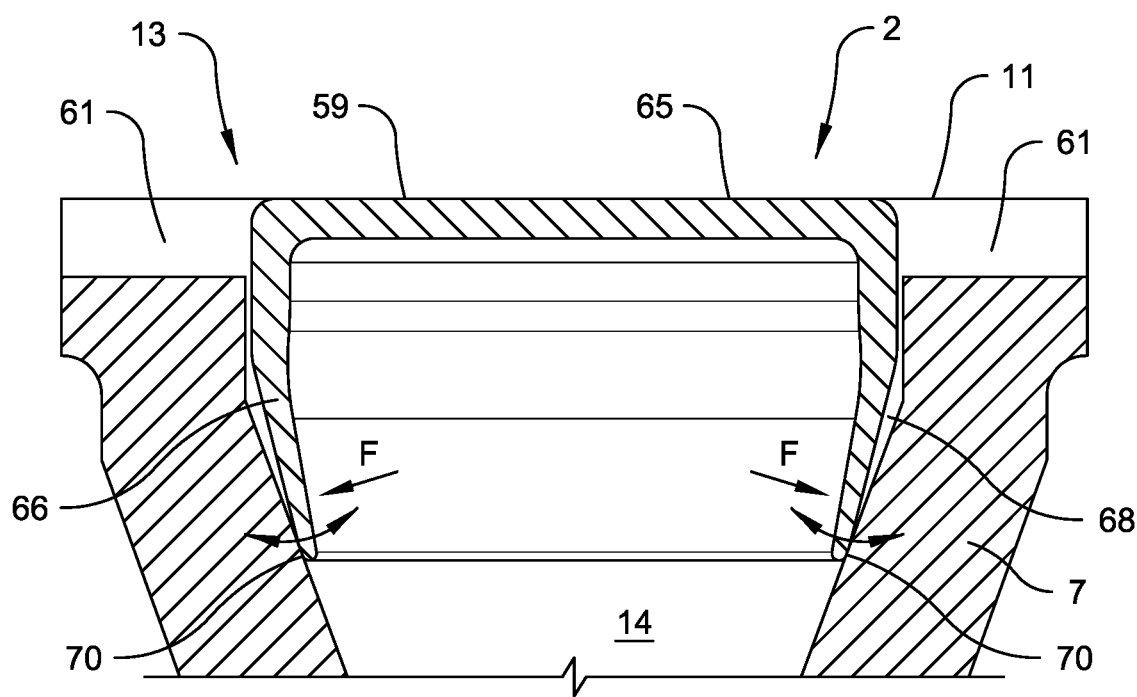
FIG. 19c is an enlarged cross-section view illustrating attachment of the cap to the plunger whereby an annular seal sealingly engages the inner surface of a side wall of the plunger so as to allow a gas to fill a first reservoir within the plunger as fluid exits the plunger in accordance with an embodiment of the invention.

Referring now to FIGS. 19*a*, 19*b*, and 19*c*, it may be advantageous for gas to enter the syringe 1 through at least one inlet operable via a cap-like structure, either in addition to or in place of the inlet(s) 18. The operable cap 59 is secured within an opening 64 along the proximal wall 11 at the proximal end 13 of the plunger 2. The cap 59 may include a center wall 65 with an annular seal 66 extending from the circumference along one side of the center wall 65. In some embodiments, the cap 59 may be attached to the proximal wall 11 via an optional hinge 60. In yet other embodiments, the proximal wall 11 may include one or more optional channels 61 radially oriented with respect to an outer diameter 62 and an inner diameter 63 of the proximal wall 11. The channel(s) 61 may facilitate flow of a gas into the plunger 2 during extension of the plunger 2 from the syringe 1 by providing a pathway that communicates with the inlet(s) 68 formed by the cap 59 with respect to the side wall 7 of the plunger 2.

Referring now to FIGS. 19*b* and 19*c*, the cap 59 is pressed into the opening 64 so that outer surfaces of the center wall 65 and the proximal wall 11 are generally aligned. The upper portion of the annular seal 66 is disposed within the opening 64 so as to form a gap between the outer surface of the annular seal 66 and the inner surface of the side wall 7. The gap forms at least a portion of the inlet 68. The lower portion of the annular seal 66 contacts and thereby interacts with the side wall 7 of the plunger 2. In preferred embodiments, the annular seal 66 should elastically deform at the contact 70 with the side wall 7 so as to maintain a force (F) which both secures and seals the cap 59 to the side wall 7. The annular seal 66 is both deformable and resilient to facilitate opening and closing functionality for proper operation of the inlet 68. In this arrangement, the inlet 68 traverses a portion of the annular seal 66 so that the inlet 68 is initially closed. In some embodiments, the force (F) may also include a force component imposed by fluid residing within the first reservoir 14.

Referring again to FIG. 19*c*, the cap 59 is operable so that the inlet 68 is opened during extension of the plunger 2 from the syringe 1. During extension, a vacuum is formed adjacent to the annular seal 66 which negates the force (F) so that at least one or more portions of the annular seal 66 moves away from the inner surface of the side wall 7 thereby providing an unobstructed pathway to complete one or more inlets 68. It is possible for a single circular opening between the annular seal 66 and the side wall 7 to define one inlet 68 or one or more separately disposed arc-shaped gaps between the annular seal 66 and the side wall 7 to define one or more inlets 68. The fully formed inlet(s) 68 permits gas external to the plunger 2 to flow into the first reservoir 14. In some embodiments, the gas may continuously flow into the first reservoir 14 during extension of the plunger 2. In other embodiments, the gas may intermittently flow into the first reservoir 14, in a burp-like fashion, as the annular seal 66 unseats to open the inlet(s) 68 and reseats to close the inlet(s) 68 in a repeating fashion. The resultant pathway facilitating flow into the first reservoir 14 may further include the optional channel(s) 61.

Referring again to FIG. 19*c*, the cap 59 is also operable so that the inlet(s) 68 is closed during retraction of the plunger 2 into the barrel 3. The force (F) may also include a force component imposed by gas residing within the first reservoir 14 that further prevents gas from leaking out of the first reservoir 14 and that further prevents fluid from leaking back into the first reservoir 14.

As is evident from the explanation herein, the described invention is a telescoping syringe which may be applicable to storing and dispensing a variety of fluids including, but not limited to, medications, adhesives, solvents, and cleaners.

The description above indicates that a great degree of flexibility is offered in terms of the present invention. Although various embodiments have been described in considerable detail with reference to certain preferred versions thereof, other versions are possible. Therefore, the spirit and scope of the appended claims should not be limited to the description of the preferred versions contained herein.

What is claimed is:

1. A telescoping syringe comprising:
   (a) a valve including a barrier, at least one outlet through said barrier, and an annular extension extending from one side of said barrier, said annular extension disposed about said at least one outlet;
   (b) a plunger including a proximal wall fixed at a proximal end of a first side wall and at least one inlet, said valve contacts a distal end of said first side wall so that said annular extension slidingly engages said first side wall, a circumferential end of said first side wall contacts said barrier to close said at least one outlet when said annular extension is biased toward a first position defined by a proximal shoulder along said first side wall and said circumferential end does not contact said barrier to open said at least one outlet when said annular extension is biased away from said first position, said annular extension contacts said proximal shoulder at said first position to close said at least one inlet and does not contact said proximal shoulder when not at said first position to open said at least one inlet, a first reservoir defined by said first side wall, said proximal wall, and said valve, said at least one inlet permits a gas to enter said first reservoir as a fluid is transferred through said valve to a second reservoir; and (c) a barrel including a second side wall with a distal wall at one end and an open end at another end, said plunger extendable from and retractable into said barrel at said open end via slidable engagement between said first side wall and said second side wall, said second reservoir defined by said distal wall, said second side wall, and said valve when said plunger is extended from said barrel.

2. The telescoping syringe of claim 1, wherein said at least one inlet is disposed along said proximal wall.

3. The telescoping syringe of claim 2, wherein said at least one inlet is a check valve secured within an opening along said proximal wall, said check valve prevents said gas from exiting said first reservoir when said fluid is transferred out of said second reservoir as said plunger is retracted into said barrel.

4. The telescoping syringe of claim 1, wherein said at least one inlet is disposed along said first side wall.

5. The telescoping syringe of claim 4, wherein an annular sealing ring disposed along said second side wall sealingly engages said at least one inlet when said plunger is retracted within said barrel.

6. The telescoping syringe of claim 5, wherein said annular sealing ring does not sealingly engage said at least one inlet when said plunger is extended from said barrel.

7. The telescoping syringe of claim 4, wherein said annular extension slidably overlays said at least one inlet.

8. The telescoping syringe of claim 7, wherein an annular flange along said annular extension seals and unseals said at least one inlet.

9. The telescoping syringe of claim 1, wherein said gas enters said plunger at one location and then said gas enters said first reservoir at another location.

10. The telescoping syringe of claim 9, wherein said inlet partially traverses said first side wall from said first reservoir to a passageway, said passageway passes through said first side wall from said proximal shoulder to said inlet, said passageway closed when said valve retracted on said plunger, said passageway open when said valve extended from said plunger.

11. The telescoping syringe of claim 10, wherein a gap is disposed between said first side wall and said second side wall, said gas does not pass through said gap into said passageway when said passageway is closed, said gas passes through said gap into said passageway when said passageway is open.

12. The telescoping syringe of claim 1, wherein said at least one inlet is disposed along said proximal shoulder.

13. The telescoping syringe of claim 1, further comprising:
(d) a break-away valve disposed within a nipple fixed to said barrel.

14. The telescoping syringe of claim 1, further comprising:
(d) a diaphragm attached to said barrel for sealing a nipple fixed to said barrel.

15. The telescoping syringe of claim 1, further comprising:
(d) a stop disposed within a nipple fixed to said barrel which permits said fluid to traverse and exit said nipple.

16. The telescoping syringe of claim 1, further comprising:
(d) a filter element disposed on said telescoping syringe which filters said gas prior to entering said at least one inlet.

17. The telescoping syringe of claim 1, further comprising:
(d) a biasing mechanism which permits said valve to extend from said plunger as said plunger is extended from said barrel and then causes said valve to retract onto said plunger.

18. The telescoping syringe of claim 17, said biasing mechanism includes an elastic annular flange along said valve which interacts with said plunger.

19. A telescoping syringe comprising:
(a) a valve including a barrier, at least one outlet through said barrier, and an annular extension extending from one side of said barrier, said annular extension disposed about said at least one outlet;
(b) a plunger including a proximal wall fixed at a proximal end of a first side wall and at least one inlet, said valve contacts a distal end of said first side wall so that said annular extension slidingly engages said first side wall, a circumferential end of said first side wall contacts said barrier to close said at least one outlet when said annular extension is biased toward a first position and said circumferential end does not contact said barrier to open said at least one outlet when said annular extension is biased away from said first position, said first position defined by a proximal shoulder along said first side wall wherein said at least one inlet closed when said annular extension is biased toward said proximal shoulder and said at least one inlet open when said annular extension is biased away from said proximal shoulder, a first reservoir defined by said first side wall, said proximal wall, and said valve, said at least one inlet permits a gas to enter said first reservoir as a fluid is transferred through said valve to a second reservoir; and
(c) a barrel including a second side wall with a distal wall at one end and an open end at another end, said plunger extendable from and retractable into said barrel at said open end via slidable engagement between said first side wall and said second side wall, said second reservoir defined by said distal wall, said second side wall, and said valve when said plunger is extended from said barrel.

20. The telescoping syringe of claim 19, wherein said at least one inlet is disposed along said proximal wall.

21. The telescoping syringe of claim 19, wherein said at least one inlet is disposed along said first side wall.

22. The telescoping syringe of claim 19, wherein said gas enters said plunger at one location and then said gas enters said first reservoir at another location.

23. The telescoping syringe of claim 19, wherein said at least one inlet is disposed along said proximal shoulder.

* * * * *